United States Patent
Cancelos et al.

(10) Patent No.: US 12,296,200 B2
(45) Date of Patent: May 13, 2025

(54) METHOD AND SYSTEM FOR INCREASING THE GAS-DISSOLUTION RATE OF A BUBBLE IN A LIQUID MEDIA VIA NON-INVASIVE RESONANT ACOUSTIC PRESSURE

(71) Applicant: University of Puerto Rico, San Juan, PR (US)

(72) Inventors: Silvina Cancelos, Mayaguez, PR (US); Manuel Rivera Bengochea, San Juan, PR (US); Edwin Lopez Ramos, Hatillo, PR (US); William Garcia, Mayaguez, PR (US)

(73) Assignees: University of Puerto Rico, San Juan, PR (US); SIL Technologies LLC, Rincon, PR (US)

( * ) Notice: Subject to any disclaimer, the term of this patent is extended or adjusted under 35 U.S.C. 154(b) by 915 days.

(21) Appl. No.: 17/324,046

(22) Filed: May 18, 2021

(65) Prior Publication Data

US 2021/0353968 A1 Nov. 18, 2021

Related U.S. Application Data

(60) Provisional application No. 63/026,462, filed on May 18, 2020.

(51) Int. Cl.
| | | |
|---|---|---|
| *A61N 7/00* | (2006.01) | |
| *B01D 19/00* | (2006.01) | |
| *G01N 29/036* | (2006.01) | |

(52) U.S. Cl.
CPC ........... *A61N 7/00* (2013.01); *B01D 19/0078* (2013.01); *A61N 2007/0004* (2013.01); *B06B 2201/55* (2013.01); *G01N 29/036* (2013.01)

(58) Field of Classification Search
CPC .............. A61N 7/00; A61N 2007/0004; B01D 19/0078; B06B 2201/55; B06B 1/0246; B06B 2201/76; B06B 1/0651; G01N 29/036; G01N 29/2437
See application file for complete search history.

(56) References Cited

U.S. PATENT DOCUMENTS

| | | | |
|---|---|---|---|
| 2012/0209116 A1* | 8/2012 | Hossack | A61M 25/00 604/23 |
| 2016/0206867 A1* | 7/2016 | Hossack | A61M 37/00 |
| 2017/0254781 A1* | 9/2017 | Spencer | B03D 1/028 |

* cited by examiner

*Primary Examiner* — Joel Lamprecht
(74) *Attorney, Agent, or Firm* — Aldarondo IP LLC; Carlos A. Aldarondo-Lopez

(57) ABSTRACT

An acoustic technique designed to increase the gas-dissolution rate of a bubble in a liquid media is proposed. Increased gas-dissolution rate is achieved by increasing the bubble's surface-to-volume ratio via bubble fragmentation. This is achieved by attaching an electroacoustic transducer to the system or load in which bubbles travel and exciting the transducer at the frequency of resonance. The electric resonance of the transducer attached to the system corresponds in frequency to the mechanical resonance of the system or load which allows for achieving such state without the use of an internally placed hydrophone to certify the resonance state. The acoustic bubble fragmentation technique increased the dissolution rate 4 to 5 times of bubbles with initial diameters between 150 and 550 μm in distilled water and in medical grade saline solution.

4 Claims, 18 Drawing Sheets

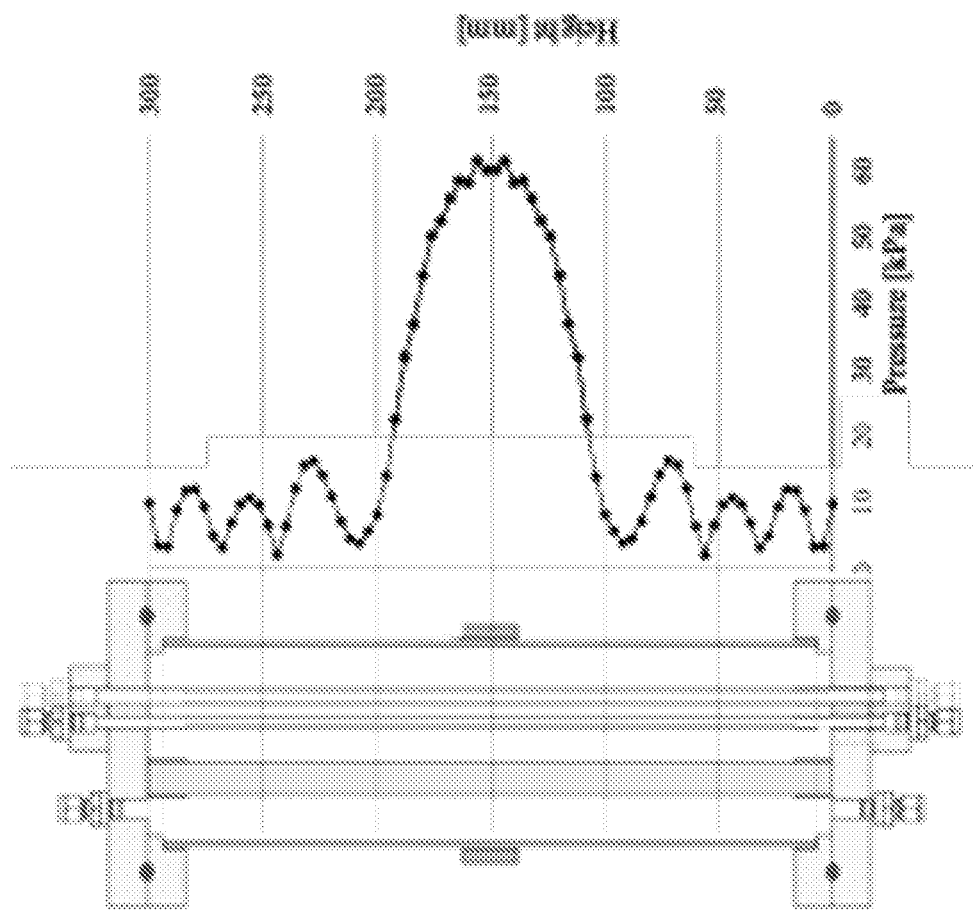

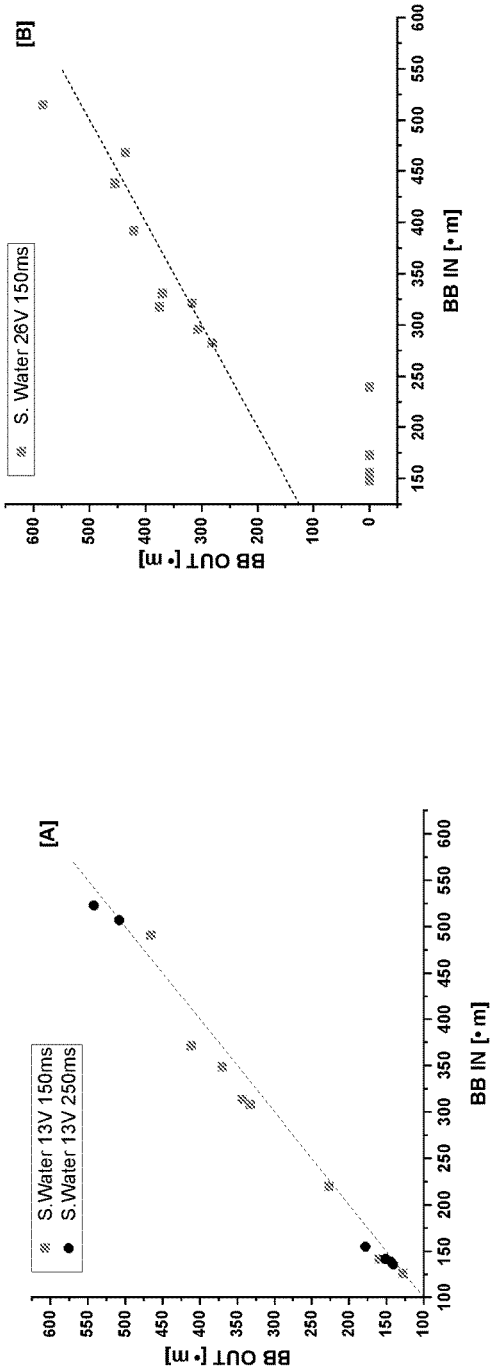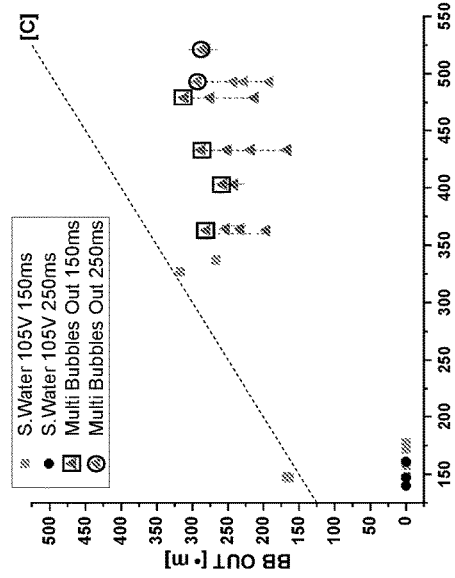
Figure 8A
Figure 8B
Figure 8C

METHOD AND SYSTEM FOR INCREASING THE GAS-DISSOLUTION RATE OF A BUBBLE IN A LIQUID MEDIA VIA NON-INVASIVE RESONANT ACOUSTIC PRESSURE

GOVERNMENT INTEREST

This invention was made with government support under grant R43 HL139289 awarded by the National Institutes of Health (NIH). The Government has certain rights in this invention.

BACKGROUND OF THE INVENTION

Bubbles are studied in different disciplines, both in natural sciences and engineering, and in the development of bubble-related technologies. For example, knowledge of bubble populations is required for most filling operations in the paint, food, detergent, and cosmetic industries, where bubbles may degrade the final product. In the oil industry, timely detection of high-pressure gas pockets provides the necessary warnings against cavitation needed to safely and efficiently extract the crude oil. In Ecology and Climate Science, proper modeling and bubble detection technology are required to understand the flux of greenhouse gasses such as methane and carbon dioxide between the ocean and the atmosphere. Even in experimental cosmology, as the acoustic emission from bubble formation is used as a signature for the detection of weakly interacting massive particles, the so-called WIMPS, the leading theoretical explanation for dark matter.

Bubble dynamics is of particular interest in many medical and biological topics. The study of cavitation, and its potential detrimental effects on nearby surfaces or tissues, has been a growing topic since it caught attention during the mid-1800s as powerful erosion was observed in ship propellers and attributed to inertial cavitation of bubbles. An important realization of this early hydrodynamically induced cavitation was the realization that bubbles strongly interacted with acoustic fields which could induce inertial cavitation. This marked the onset of the field of ultrasonics. Since then, a wide range of ultrasonic sub-fields and applications have emerged such as ultrasonic bubble excitation for breakup of kidney stones, drug delivery using bubble capsules, high contrast medical imaging, sonochemistry, among others.

Much of what is known about the complex dynamics of the fluid-gas interphase of bubbles as they react to perturbations of acoustic or hydrodynamic origin is owed to the application of acoustic standing waves. Acoustic resonance has long been applied in the study of cavitation thresholds of liquids for its ability to generate high-intensity acoustic pressures in a small region. Additionally, resonant cavities have been extensively applied as bubble acoustic traps and levitators, as for a given bubble size there exists a set of parameters (frequency, acoustic intensity, bubble position at the onset of the standing wave, liquid gas saturation level, etc.) that will fix the bubble's position at the pressure antinode. This facilitates experiments regarding single bubble dynamics considerably and has allowed for the detailed study of a wide range of bubble phenomena such as the onset of nonlinear bubble oscillations, the Rayleigh collapse and shock wave emission, liquid microstreaming in the vicinity of the bubble, and the light emission generated during a sonoluminescence event. However, exploiting the capacity that a pressure standing wave has to efficiently concentrate acoustic pressure at its anti-nodes for commercial applications is rarely reported.

SUMMARY OF THE INVENTION

The invention provides a bubble fragmentation technique based on acoustic resonance of a liquid filled enclosed volume. The inventive method takes advantage of the increased acoustic pressure obtained from the pressure standing wave in the resonant chamber, as compared to the pressure amplitude obtained from a free-traveling wave, to excite bubble parametric instability modes that result in bubble fragmentation. Bubble fragmentation greatly increases the gas dissolution rate by increasing its surface to volume ratio making this technique viable as an additional line of defense in industrial or medical processes where having a bubble-free medium is of utmost importance.

According to an aspect of the invention, the method exploits the reciprocity principle of transducers to determine the mechanical resonant frequency of potentially a wide range of enclosed systems, such as tubes and even soft systems such as anatomical limbs of biological species.

According to another aspect of the invention, the inventive method is used as an emergency treatment for patients known to be at risk of developing gas embolism such as scuba divers after a fast resurfacing, or from any of numerous iatrogenic sources given that gas embolism can result from procedures in almost all clinical specialties.

BRIEF DESCRIPTION OF THE DRAWINGS

Further features and advantages of the invention will become apparent from the following detailed description taken in conjunction with the accompanying figures showing illustrative embodiments of the invention, in which:

FIG. 3D shows the acoustic pressure measured inside the SAT as function of height generated by the powered PZT at the resonant frequency.

FIG. 8A shows bubble fragmentation events with the bubble guide, or artificial artery, filled with saline solution, where the PZT was powered with 13 Vp-p and bubble fragmentation occurs in all data points below the inclined dashed line.

FIG. 8B shows bubble fragmentation events with the bubble guide, or artificial artery, filled with saline solution, where the PZT was powered with 26 Vp-p and bubble fragmentation occurs in all data points below the inclined dashed line.

FIG. 8C shows bubble fragmentation events with the bubble guide, or artificial artery, filled with saline solution, where the PZT was powered with 105 Vp-p and bubble fragmentation occurs in all data points below the inclined dashed line.

Figure 1:
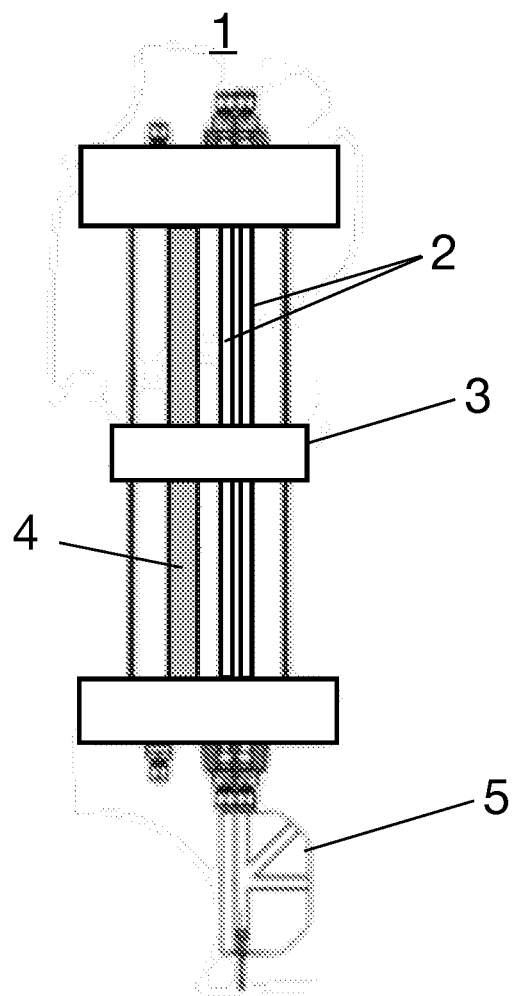
FIG. 1 illustrates the RAC used for the bubble fragmentation experiments, according to the present invention.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Materials and Methods

Resonant Acoustic Chamber (RAC) and the Principle of Reciprocity

The method according to the invention, applies the concentrated acoustic pressure obtained at the anti-node in a volume at resonance to accelerate bubble dissolution by increasing its surface-to-volume ratio via fragmentation. A key feature is to be able to function with different volumes, geometries, and materials as it adapts the frequency to obtain the resonant state. To eliminate the need of measuring with a hydrophone at different locations inside the resonant volume or load, the technique exploits the principle of reciprocity obeyed by many electroacoustic transducers. The inventors have reported in the past on the effectiveness of applying the reciprocity principle in different systems to non-invasively induce and determine a state of mechanical resonance. The present invention extends that previous work by including a wider range of frequencies in the numerical analysis used (Rivera M, Lopez E, Cancelos S. A non-invasive, low frequency resonant method to detect bubbles in liquid media. Appl Acoust 2021; 179:108044 and Rivera M, Lopez E, Cancelos S, Marin C. Low-power gas microbubble detection technology based on acoustic resonance. Engineering Reports. 2021; e12401, both incorporated herein in their entirety).

Originating from Lord Rayleigh's analysis of the reciprocal theorem of mathematical physics, the principle of reciprocity is the principle that establishes that the complex ratio of force to velocity is analogous to the complex ratio of voltage to current. This provides a basis for using the methods of electric circuit analysis in describing and analyzing the electro-mechanical behavior of electroacoustic transducers. The task is therefore reduced to finding an equivalent electric circuit that can represent the electric and mechanical driving sources and impedances with a combination of passive RLC elements. Finding an equivalent circuit that accurately represents the motional and electrical components of a transducer is not always a simple task; solutions are not unique, equivalence might be frequency dependent, and normally considers only one degree of freedom of the transducer. However, for a piezoelectric (PZT) transducer driven by a single dominant mode of vibration, a simple RLC circuit, known as the Van Dyke circuit, can adequately model the transducer and key information can be obtained from it. Its most basic form, which assumes a very large internal electrical resistance, consists of serially connected RLC elements in shunt with a capacitor. The RLC elements represent the motional impedance of the system while the shunt capacitor is the intrinsic capacitance of the piezoelectric. The complex input electrical admittance, Y, of the Van Dyke circuit becomes the sum of the electrical ($Y_E$) and motional admittance ($Y_m$):

$$Y(f) = Y_E + Y_M = j2\pi f C_0 + \cfrac{1}{R + j\left(2\pi f L - \cfrac{1}{2\pi f C}\right)} \quad (1)$$

which has a motional resonance when the real part, the conductance, is maximum:

$$f_r = \frac{1}{2\pi}\sqrt{\frac{1}{LC}} \quad (2)$$

The model applies in the vicinity of electric resonance modes and has the powerful feature, as seen from equation (2), that the inductive and capacitance elements take into account not only the mechanical contribution of the PZT itself, but also any inertial load it is mechanically coupled with. Therefore, voltage and current measurements of the electrical terminals of a PZT during a frequency sweep can potentially determine the motional resonance frequency of any system attached to the transducer. Underwater transducers and sonar frequently take advantage of this to determine adjustments required to operate underwater as compared to air, but there are scarce reports on applications of this principle to determine and investigate the mechanical resonant state of more complex inertial loads.

In the present invention, a PZT will be applied as a single emitter/receiver unit allowing the usage of the response signal, in the form of current and phase angle between current and supplied voltage at the transducer, to be used as a proxy measurement to determine the resonant state of a chamber. As in the inventor's previous work, a resonant acoustic chamber (RAC) was used with dimensions similar to that of an average human thigh. A schematic diagram of the constructed RAC is presented in FIG. 1. It consists of an open-ended, 5 mm thick, cylindrical Borosilicate glass (1) with an outer diameter of 95 mm and 300 mm in length. This glass cylinder is capped at its ends by two Plexiglas acrylic flanges in which all necessary fittings were incorporated while providing structural integrity to the unit. Inside the glass cylinder, two vinyl tubes traversing the length of the cylinder attached to fittings on the flanges, serve as bubble guides (2) through the resonant volume when injected by a bubble injector (5). In order to generate the acoustic field in the chamber's volume, a 25 mm wide and 12 mm thick radially polarized PZT piezoelectric (3) from Sensor Technology, LTD, Canada was fixed at mid-height of the cylinder using Stycast™ 1264 epoxy (Emerson & Cumming, Billerica, MA, USA). To further challenge the robustness of the prototype device and mimic real-world conditions of potential applications, a rigid and cylindrical (15 mm in diameter) polyurethane Fourth Generation Cancellous simulated bone (4) was also attached to the top and bottom flanges. The entire RAC's volume, including the interior of the vinyl tubing, is vacuum filled with degassed water.

Simulation Results and Validation

Figure 2:
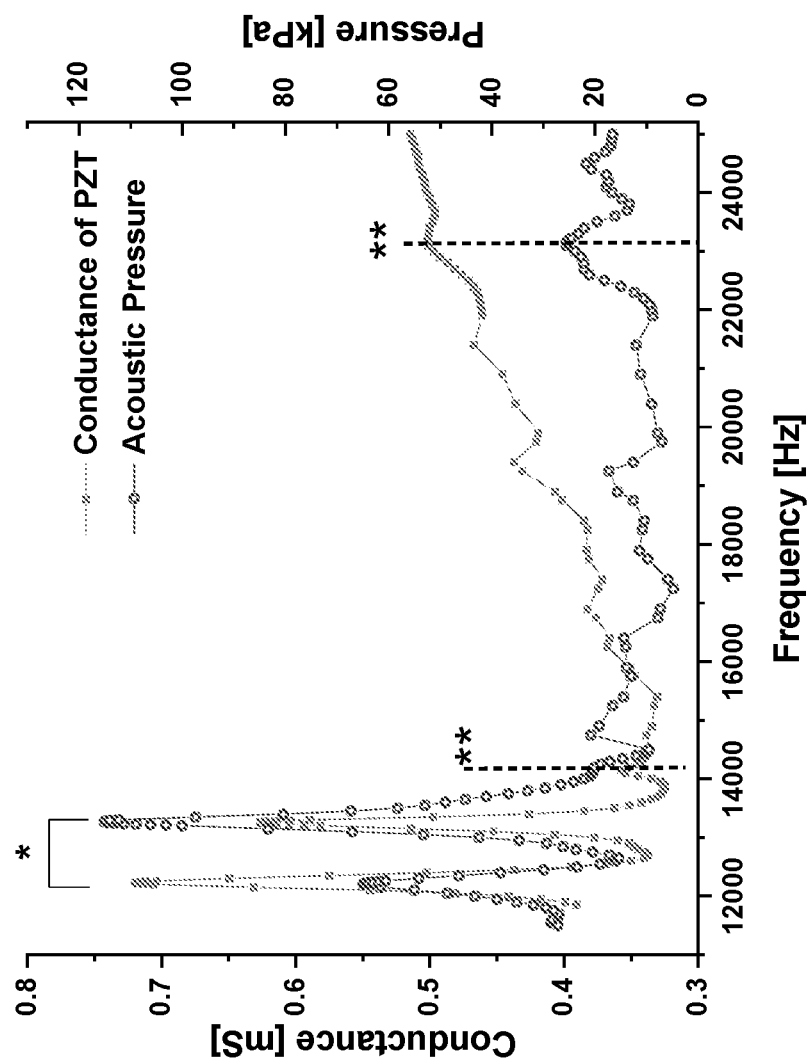
FIG. 2 shows the simulated frequency response of the conductance of the PZT and the acoustic pressure generated at the center of the RAC, according to the present invention.

To test the validity of using the reciprocity principle in our system as a means to noninvasively determine the mechanical resonant state, numerical simulations were carried out with COMSOL Multiphysics. The geometry of the water-filled resonant chamber with an equivalent PZT acoustic source was generated and the conductance and acoustic pressure spectra were obtained via a finite element method. The acoustic field in the fluid domain was determined from the solution of the inhomogeneous Helmholtz equation while the solid domain was solved with structural equations coupled with constitutive relationships for modeling piezoelectricity. FIG. 2 shows the conductance and pressure results obtained from COMSOL at the center of the simulated RAC in the frequency range of 11500-25000 Hz.

According to the simulation, several peaks of both conductance and pressure appear within this frequency range. The two outstanding peaks, identified with a single asterisk, are obtained at 12240 Hz and 13260 Hz respectively. The first one has a conductance local maximum of around 0.71 mS and a corresponding acoustic pressure of 65 kPa. The second peak in the single asterisk bracket has a conductance of 0.63 mS and the corresponding acoustic pressure of 114 kPa. At least two additional conductance peaks, identified with double asterisks, can be identified in FIG. 2. Close inspection reveals that these two peaks, positioned at 14150 Hz and 23,140 Hz, also coincide in frequency with local maxima in acoustic pressure generated within the RAC. Therefore, it appears from the simulation that each local conductance maxima correspond in frequency to a local maximum of acoustic pressure generated at the center of the RAC as expected from invoking the reciprocity principle.

The results of the numerical analysis around the frequency of 13260 Hz, where the simulation predicted that a maximum acoustic pressure would be generated, were validated with direct pressure measurements using a subminiature pressure hydrophone sensor (PCB Piezoelectronics, Depew, NY). The PZT was harmonically driven through the radial thickness using a 33220A Agilent voltage wave generator (Agilent Technologies, Inc., Santa Clara, CA, USA) connected to a 20× voltage amplifier (EPA102, Piezo Systems Inc., Cambridge, MA). The voltage (V), current (I), and phase lag ($\varphi$) on the PZT as a function of frequency, as well as the readings from the hydrophone, were recorded using an oscilloscope (54615B Agilent Technologies, Inc., Santa Clara CA, USA) with a GPIB interface (GPIB-USB-B_488.2, National Instruments, Austin, TX, USA) and a 1.25 MSamples/s DAQ (USB 3656, National Instruments, Austin, TX, USA) connected to a personal computer. The entire process was controlled through a LabView algorithm. The complex impedance (Z) and admittance (Y) frequency dependency can then readily be calculated by using the relationships $Y=1/Z=I/V$.

Figure 3A:
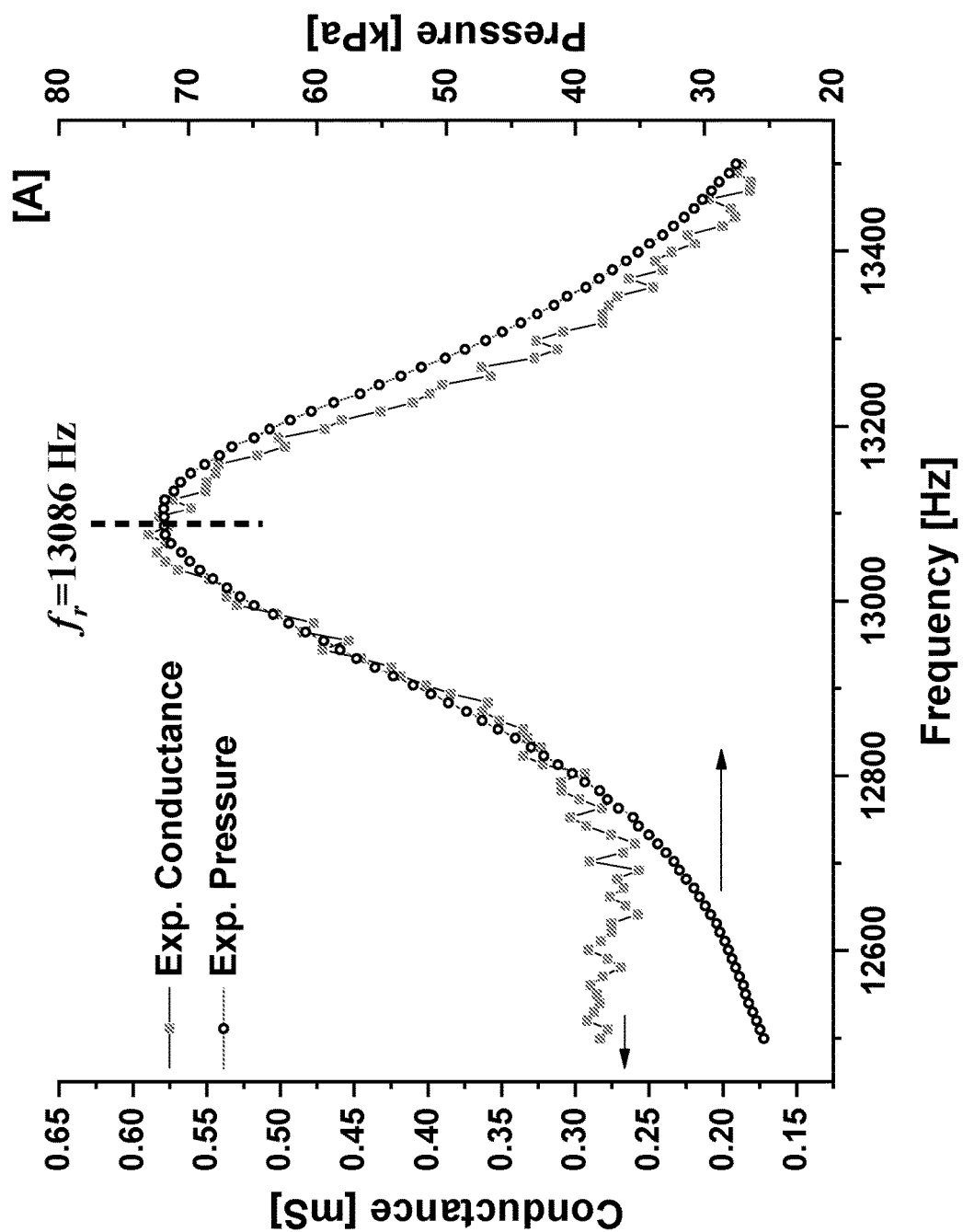
FIG. 3A shows the experimentally determined values of narrow frequency response of the conductance and the acoustic pressure generated at a position radially off-centered.
Figure 3B:
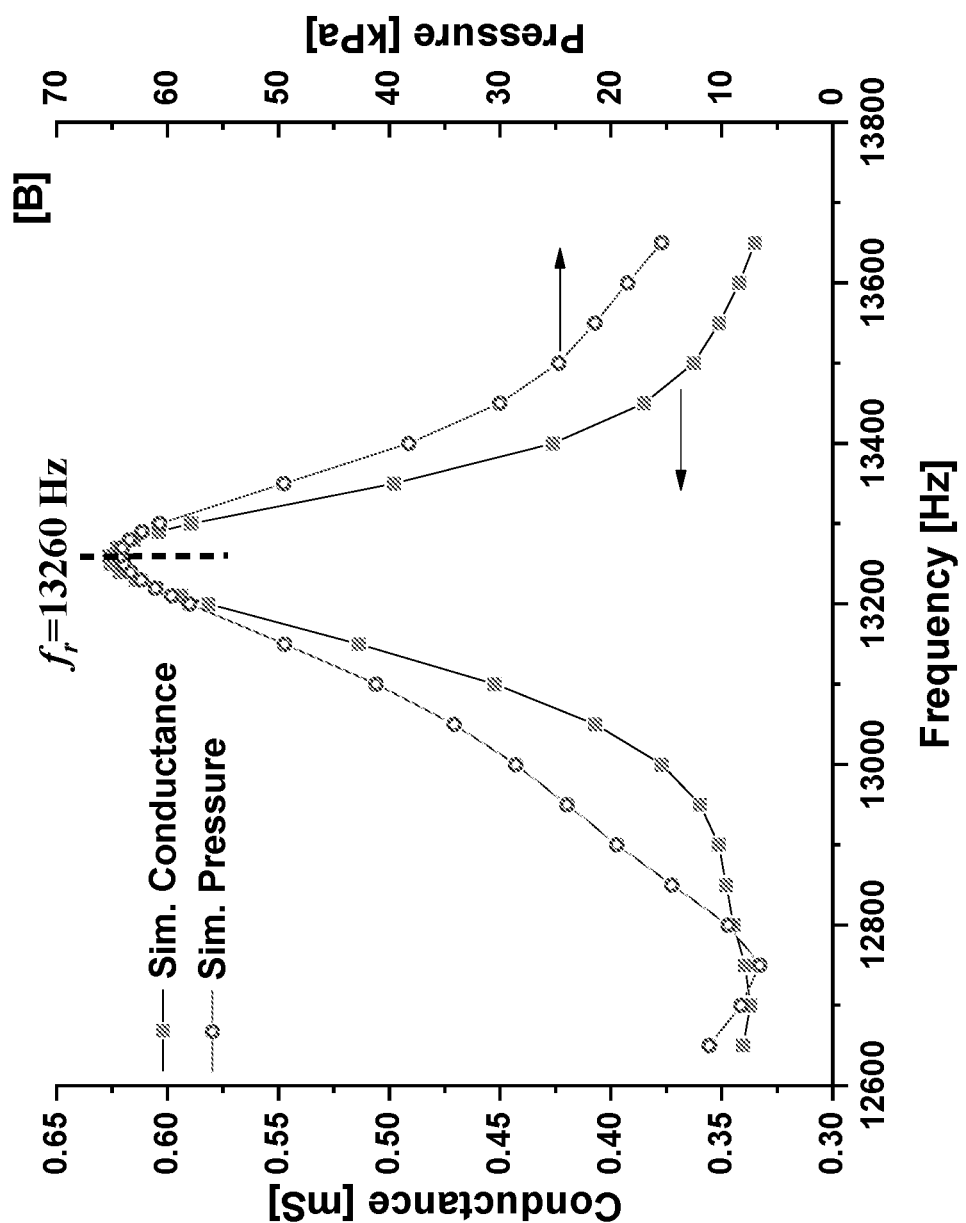
FIG. 3B shows the results obtained from the simulation of narrow frequency response of the conductance and the acoustic pressure generated at a position radially off-centered.
Figure 3C:
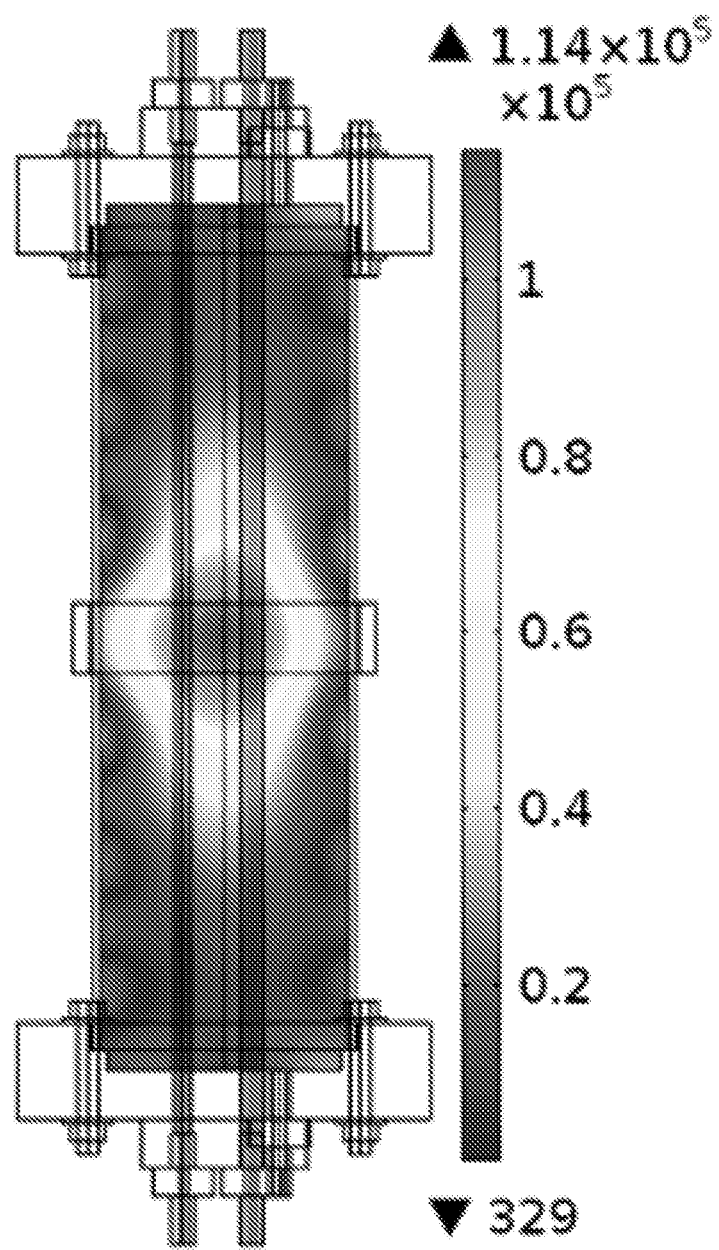
FIG. 3C illustrates the acoustic pressure distribution along a vertical plane that passes through the center of the RAC when operated at resonance.

FIGS. 3A-3B compare the measured acoustic pressure and conductance spectra with those obtained from the simulation in the vicinity of maximum pressure as determined by the simulation (FIG. 2). The acoustic pressure in FIG. 3A was measured with the hydrophone positioned at the RAC's mid-height and radially slightly off-center. The corresponding pressure values obtained from the simulation are presented in FIG. 3B and were also calculated at this off-center position which are expected to be lower than those calculated at the geometric center of the RAC and presented in FIG. 2. The experimental data shown in FIG. 3A confirms that the RAC obtains a maximum pressure concentration when the PZT is driven at its electrical resonance frequency. The resonance frequency of the system obtained from experimental measurements was 13086 Hz while from the simulation a result of 13260 Hz was observed, less than 2% difference. FIG. 3C is a visual representation of the pressure profile predicted by the simulation at the resonance frequency showing how the acoustic pressure within the volume is spatially concentrated at the center. These results were experimentally confirmed, and the results are presented in FIG. 3D, where the pressure peaks represent the antinodes of the standing wave.

Consequently, the reciprocity principle proved valid in the current multi-component mechanical load of the transducer even with elements that contributed to the reduction in symmetry such as the off-center artificial bone. The significance is that measuring the electrical input of the loaded PZT can be used to identify the resonance frequency of the RAC without the need of a hydrophone, which requires internal volume access, and the system can be quickly recalibrated as frequently as desired.

Bubble Fragmentation Experimental Method

Experiments were carried out to produce bubble fragmentation by taking advantage of the concentrated pressure produced by the standing wave when the RAC is operated at resonance. Bubble fragmentation has the effect of accelerating the gas dissolution rate by increasing the surface-to-volume ratio. For this purpose, an experimental setup as the one depicted in FIG. 4 was used. The basic methodology consisted of the following steps: First, a frequency sweep on the PZT (3) is performed to determine the system's resonant frequency, defined as the electric resonance of the PZT mechanically coupled with the RAC (as explained on patent U.S. Pat. No. 10,376,244 B1 issued on Aug. 13, 2019 to Cancelos, et al., incorporated herein in its entirety). Then the needle or capillary and the air pressure applied are calibrated to consistently produce single bubbles of desired sizes. Once this is achieved, bubbles are injected and recorded by Camera #3 for size analysis. These bubbles rise by buoyancy reaching the PZT's action zone at which point the PZT is actuated and, finally, bubble fragments that reach the outlet pool (6) are recorded by camera #1 for further size analysis. The entire set-up is powered and controlled with the equipment previously described.

Results and Discussion

Figure 4:
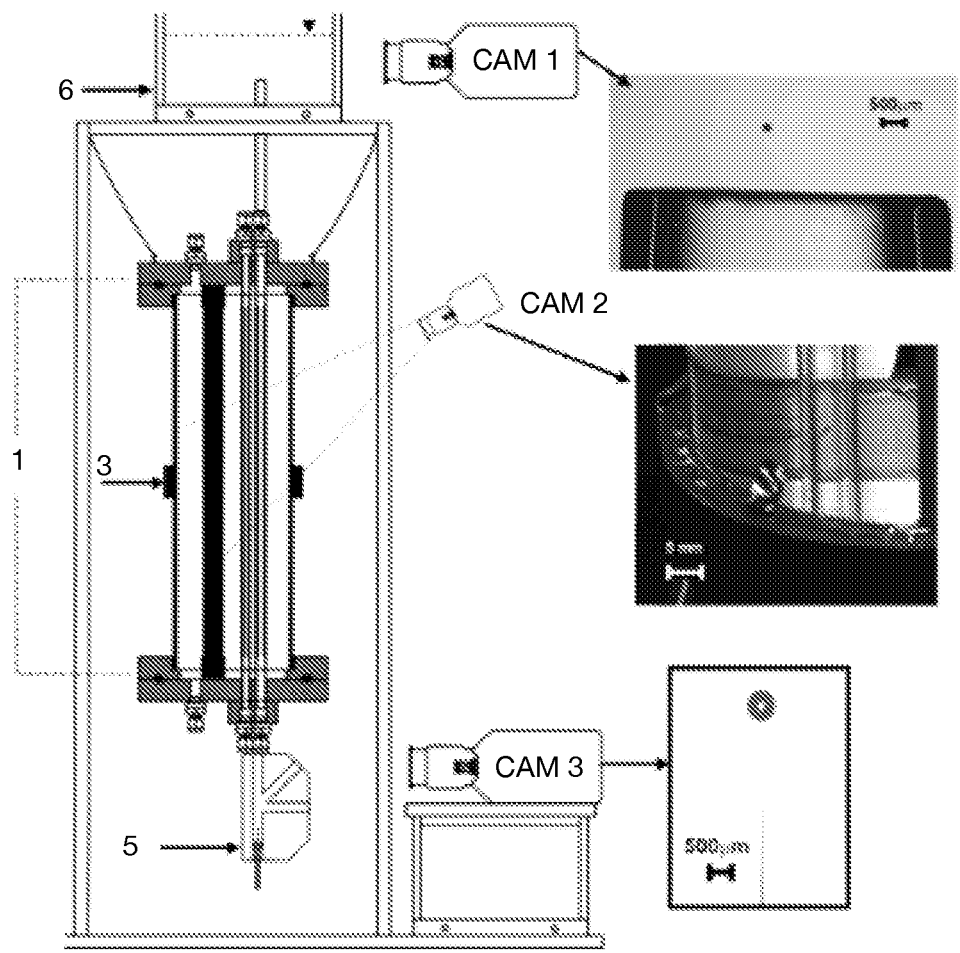
FIG. 4 shows a schematic of the experimental set-up used in the bubble fragmentation experiments.
Figure 5:
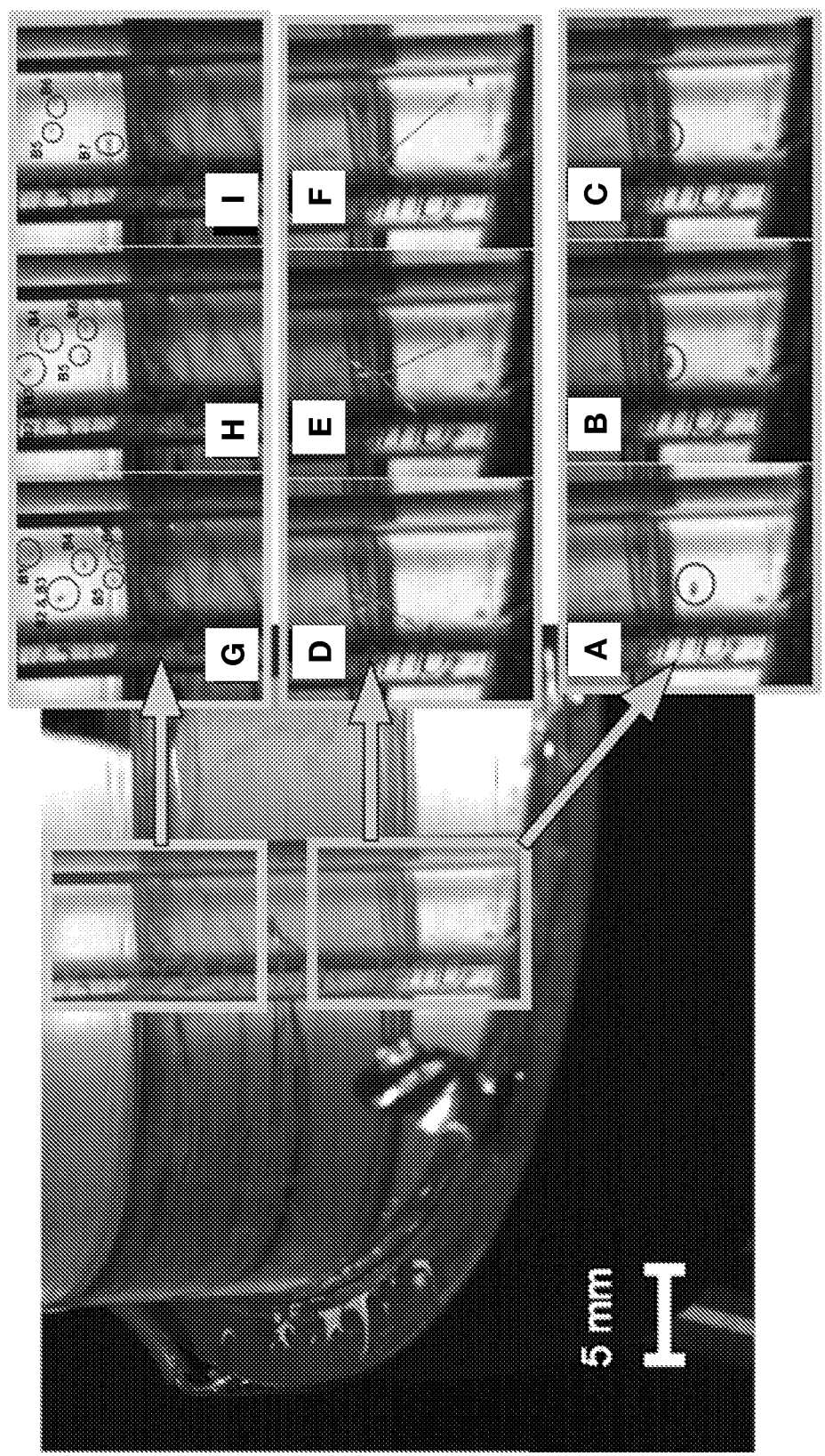
FIG. 5 shows a magnified view of the action zone of the PZT, where as the injected bubble rises by buoyancy (A, B, C), it reaches the PZT action zone (D, E, F) where it is fragmented and surviving fragments rise towards the RAC's outlet (G, H, I) where they are recorded for size analysis.

Bubble Fragmentation experiments in the RAC were carried out using the setup shown in FIG. 4. After an electrical frequency sweep, the frequency at which the PZT exhibited maximum conductance was selected and applied to the PZT during the experiments. Mechanical resonance of the system is sensitive to many uncontrolled factors such as temperature fluctuations and material fatigue, however, determining the resonance frequency through the electric response of the PZT consistently served as a proxy measurement for resonance. Therefore, the exact resonance frequency varied over time in an unpredictable manner, but periodic electric frequency sweep allowed for a quick recalibration of the system which is one of the main advantages of the method. Once the resonance frequency was established, single bubbles of controlled size were injected by the bubble injector (5) into the bubble guide (2) where it approaches the height of the PZT (3) by buoyancy at which point the PZT is powered. The time the PZT (3) remained powered was varied between 150 ms and 2000 ms. When a bubble is in enough proximity to the high-pressure zone of the standing wave anti-node, depending on the medium, size of the bubble, and acoustic pressure amplitude, a bubble fragmentation event can occur. An example of such fragmentation event captured by camera #2 (CAM2) in FIG. 4, is shown in FIG. 5. In this case, a single bubble of 522 µm in diameter is injected into one of the bubble guides of the RAC. As the bubble approaches the region of action of the PZT (A, B and C on FIG. 5), the PZT is actioned for 150 ms creating the pressure standing wave which fragments the bubble (D, E and F on FIG. 5). The remaining fragments continue the upward motion by buoyancy after the PZT is turned off and they are recorded by Camera #3 (CAM3) for size analysis. In this example, the original 522 µm injected bubble is fragmented into 7 smaller bubbles with diameters of 268 µm, 245 µm, 262 µm, 229 µm, 234 µm, 195 µm and 163 µm (G, H, and I on FIG. 5). The total gas volume contained in bubbles recorded by Camera #3 (CAM3) at the RAC's outlet was 62% of the gas volume contained in the original 522 µm injected bubble. The difference is attributed to gas dissolution in the liquid or bubble fragments smaller than 50 µm which dissolve in less than a minute. Besides the quasi-instantaneous dissolution of 38% of the total gas injected in bubble form, the residual bubble fragments will naturally dissolve on their own much faster than the original bubble. For example, according to the Epstein-Plesset bubble stability model the largest fragment in this case, which was a 268 µm bubble, is estimated to take 30 minutes to dissolve compared to 156 minutes that would take for the original 522 µm to dissolve.

Applying different powers to the PZT for several time intervals, experiments of this sort were performed in the RAC with the bubble guide containing distilled water or a 0.9% wt medical grade saline solution.

Figure 6B:
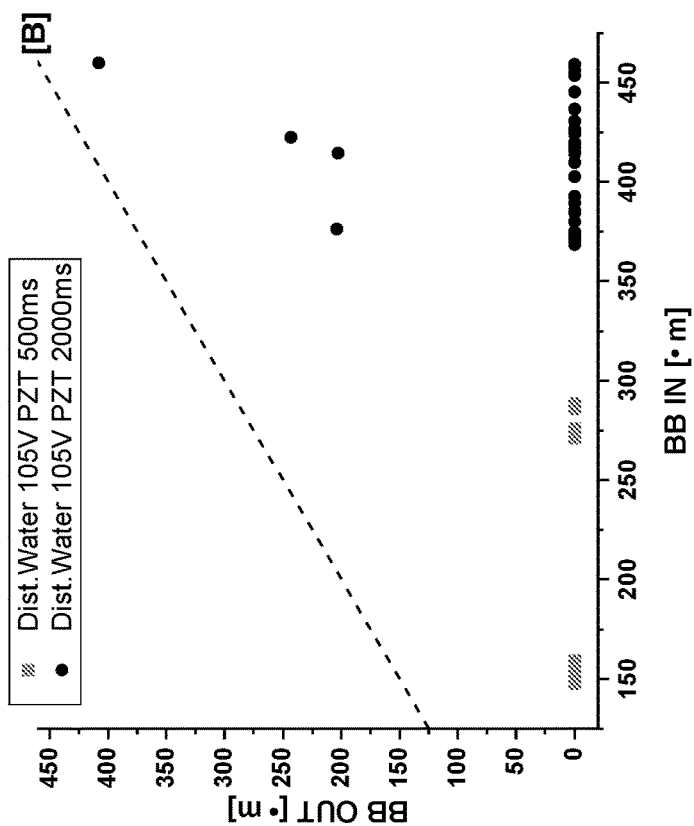
FIG. 6B shows bubble fragmentation events with the bubble guide, or artificial artery, filled with distilled water, where the PZT was powered with 105 Vp-p and bubble fragmentation occurs in all data points below the inclined dashed line.
Figure 6A:
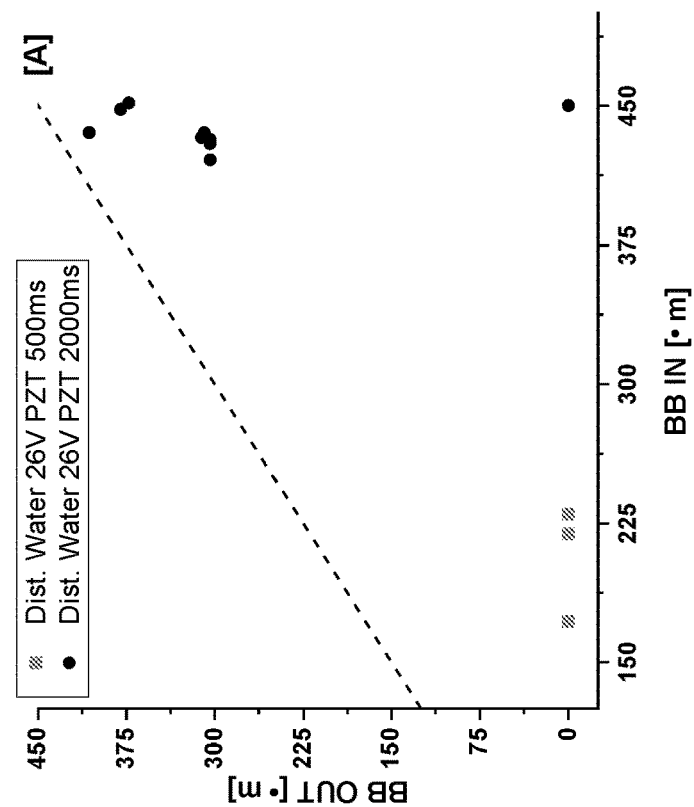
FIG. 6A shows bubble fragmentation events with the bubble guide, or artificial artery, filled with distilled water, where the PZT was powered with 26 Vp-p. Bubble fragmentation occurs in all data points below the inclined dashed line.

FIGS. 6A, 6B summarize the bubble fragmentation results obtained from the RAC and bubbles rising in distilled water. The horizontal axis indicates the size of the bubble being injected while the vertical axis specifies the bubble size observed at the outlet after being exposed to the pressure standing wave created by the PZT when excited at the resonant frequency. The inclined line defines the fragmentation zone y=x; data points below this line indicate that fragmentation occurred while data points on or above the line correspond to cases where no fragmentation occurred. As observed in FIG. 6A, activation of the PZT with just 60 mW (26 Volts peak-to-peak) considerable bubble fragmentation is observed for bubbles of sizes below 350 µm but the effect was negligible for larger bubbles. Increasing the power supplied to the PZT to 1 Watt substantially increases the fragmentation effect and this can be observed in FIG. 6B where injected bubbles, ranging in size from 150 to 450 µm, were nearly always fragmented into smaller bubbles that naturally dissolved before being able to be detected at the outlet.

Figure 7:
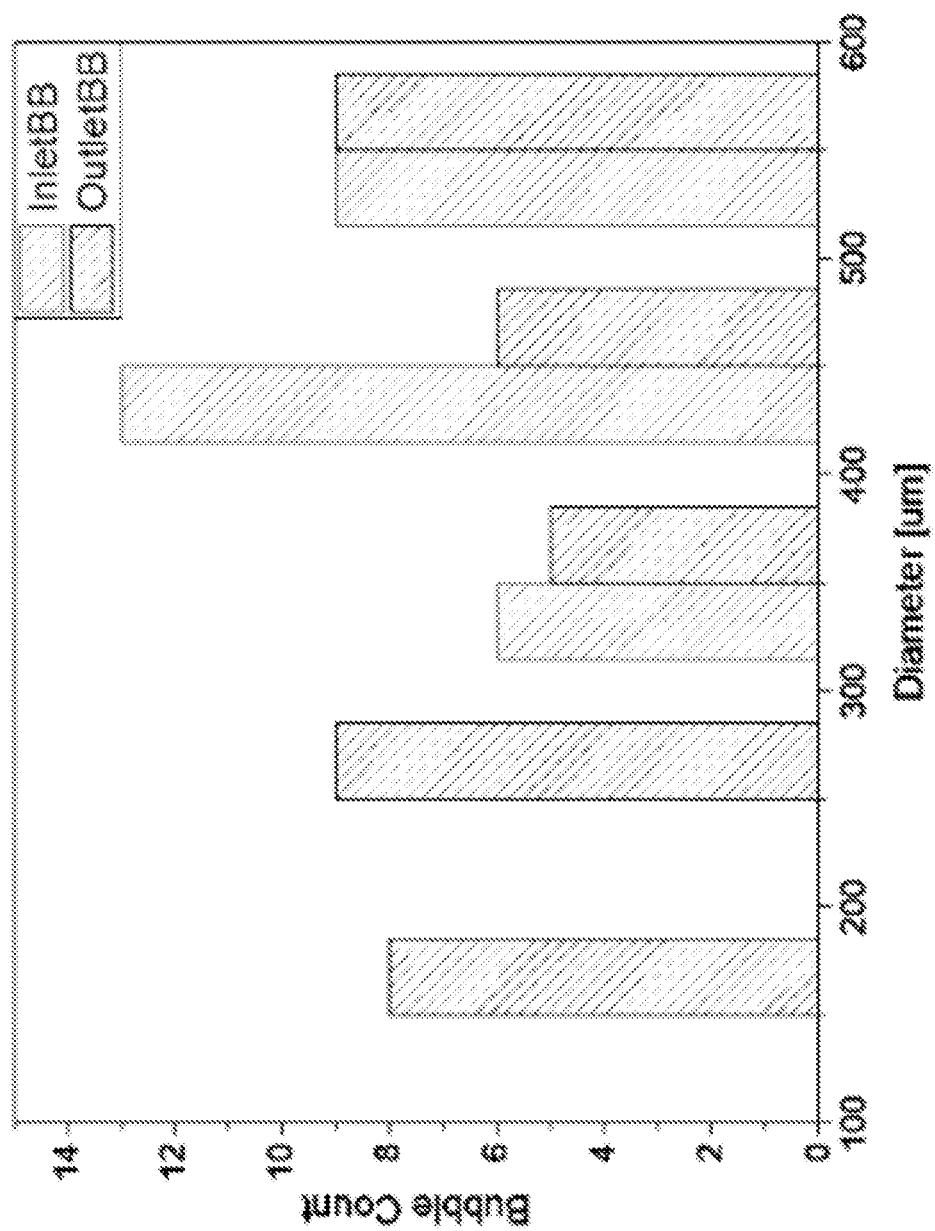
FIG. 7 shows the size distribution of bubbles injected into the SAT (Inlet BB) and bubbles observed at the outlet after fragmentation occurred (Outlet BB).

Similar to the experiment just described, tests on the RAC were performed with bubble populations. FIG. 7 shows typical results obtained for such tests. In the case presented, 28 bubbles with diameters ranging from 300 µm to 600 µm distributed according to the INLET BB distribution in FIG. 7, were introduced into the RAC's artificial artery or bubble guide. The bars labeled OUTLET BB in the graph, represent the size distribution observed and recorded by Camera #3 (CAM3) at the RAC's outlet. It is clear from the chart that the average diameter of the bubble population has decreased as a result of the PZT action, effectively decreasing the total dissolution time of such bubble population. However, the overall gas volume contained in the bubbles before and after the application of the PZT disturbance to the bubble population is not as different as that observed in the single bubble case. This is because given that there is a spread in sizes there is also a spread in rising bubble speed and as a result, many injected bubbles will be outside the PZT action zone when it is activated. In this case, footage from Camera #2 (CAM2), (which records the PZT action zone) showed that the first 9 bubbles were out of the action zone and therefore passed intact. Without taking into account these bubbles, we observe 75% of the original gas volume at the outlet, attributed to gas dissolution or fragmentation into bubbles of less than 50 µm.

To further test the resilience of the bubble fragmentation by resonance approach of the present invention, experiments were carried out in the RAC with 0.9% saline solution obtained from a local medical supply store filling up the artificial artery. The main reason for testing the RAC with saline solution is that bubble dynamics is highly dependent on the mechanical properties of the liquid medium and the saline solution simulates better conditions of blood than distilled water while remaining optically transparent. This would be relevant for applications on biospecimens.

FIGS. 8A-8C show the results obtained in the RAC with saline solution filling the artificial artery of the RAC. Same as the results presented for distilled water, the inclined straight line defines the fragmentation zone where data points below the line represent cases where fragmentation occurred. Vertical dashed lines indicate a group of fragments belonging to the same original bubble injected into the system. Bubbles generated in saline solution proved to be more resilient than in distilled water. As seen in FIG. 8B, powering the PZT with 60 mW (26 Volts peak-to-peak) fragmentation was possible only for bubbles with an initial diameter below 300 µm. Above this size, bubbles exited the RAC completely intact, in contrast to the distilled water case where some fragmentation still occurred. The results in FIG.

8A confirm that powers below 60 mW will most likely produce no fragmentation at all. As in the case of distilled water, applying 1 Watt to the PZT results in significant fragmentation. The results for 1 watt applied to the PZT, presented in FIG. 8C, reveal that bubbles injected with diameters below 250 µm were typically completely dissolved within the experimental time scale and larger bubbles (d>250 µm) tend to fragment into 2 to 5 smaller bubbles. Typical total gas dissolution of these cases ranges between 30-55% which is highly significant and even more so considering that these numbers correspond to a single pass while real-world application could consist of multiple passes. Nitrogen bubbles, for example, directly responsible for the undesired effects of decompression sickness lie within this size range.

The exact mechanism responsible for the bubble fragmentation observed is extremely difficult to determine due to the transient nature of air bubbles in a liquid. Moreover, major analytical difficulties arise naturally from first-principle bubble dynamics theoretical models. All bubble dynamic models stem from the basic Rayleigh-Plesset model. Derived from mass and momentum conservation principles, the model uses the bubble radius as a generalized coordinate with the at-rest or unperturbed equilibrium bubble radius as a boundary condition. The resulting equation governing the bubble radial dynamics is expressed as:

$$\rho R \ddot{R} + \frac{3}{2}\rho \dot{R}^2 = p_{gn}\left(\frac{R_n}{R}\right)^{3\kappa} + p_v - P_{stat} - \frac{2\sigma}{R} - \frac{4\mu}{R}\dot{R} - p(t) \quad (3)$$

Where R is the time-dependent bubble radius, $R_n$ is the bubble's rest radius, K is the polytropic exponent of the gas inside the bubble, $p_v$ is the vapor pressure, and $p_{gn}$ is the gas partial pressure in the bubble at rest and p(t) is a driving force. Dots indicate time derivatives. The critical fluid properties are contained in the fluid density ρ, the surface tension σ, and the dynamic viscosity µ. The right-hand side of the equation represents the difference between the bubble's internal pressure the external pressure in the liquid which drives the bubble's radial motion. As seen from Rayleigh's equation, the model consists of just one ordinary differential equation of second order which can be viewed as describing a nonlinear oscillator, but one with highly peculiar properties, for instance a time-dependent mass. This leads to special oscillating properties, particularly as the pressure amplitude of the acoustic forcing increases, such as chaotic radius dynamics, the fast Rayleigh-collapse, the appearance of bubble subharmonic frequencies, among others. Therefore, closed analytical solutions to the bubble models are not known except for the empty bubble and only experimental methods have revealed over time many of the sources of bubble instabilities that could lead to fragmentation, dissolution, or complete annihilation.

One of the easiest bubble instabilities onset to excite are those related to the loss of the bubble's spherical shape. Since the 1950s, it was known from observations that a stably trapped bubble in an acoustic standing wave would suddenly exhibit random positional oscillations if the acoustic pressure was increased above a certain threshold. It was proposed that bubble surface oscillations or Faraday waves appearing above the pressure threshold were responsible for the bubble's position instability. As it is well understood, a bubble's volume subjected to a low power acoustic field will pulsate with an amplitude determined by the size of the bubble and the acoustic driving frequency; obtaining a maximum when the acoustic frequency matches the bubble's breathing frequency. However, as the acoustic pressure is increased beyond a well-defined threshold, the nonlinear response of the gas bubble results in shape oscillations superimposed upon the spherical volume pulsation. Known as parametric instability (PI), since the bubble's radial dynamics act as a parametric drive, these surface oscillations can be theoretically described using Plesset-Rayleigh equation (Equation 1) assuming a nearly spherical shape with only small surface perturbations. However, the theory is incapable of describing the phenomena beyond the stability threshold where the amplitude of surface oscillations grow enough that fragmentation might occur. The minimum acoustic pressure required to excite PI behavior depends on the acoustic frequency and bubble size, being least for bubbles of resonance size, and considerably lower than the acoustic pressure required for inertial cavitation to occur. Many reports on the acoustic pressure threshold of PI are studies related to sonoluminescence, as PI is directly responsible for the restricted narrow domain in bubble radius-acoustic pressure space where stable sonoluminescence can take place. For example, it has been consistently reported that acoustic forcing at about 20 kHz can trigger PI on bubbles with radius of 8 µm when acoustic pressure is around 80 kPa. For larger bubbles and frequencies in the kHz range, the PI pressure threshold is considerably less. Typical reported value ranges are between 15 kPa and 30 kPa for bubble radius between 50 µm and 130 µm, and only a few hundred pascals for bubbles in the mm range. The amplitude of bubble surface oscillations once PI pressure thresholds are breached can accumulate after several acoustic cycles leading to fragmentation. Not too far from resonance size, as in the present invention, the PI pressure threshold for bubbles above resonance size has been reported to be slightly less to those bubbles below resonance. This is because bubbles smaller than resonance size oscillate enough to create PI while larger ones oscillate less but the reduced surface tension makes it easier to produce surface instabilities.

In the present invention, because the experimental setup excludes the possibility of having bubble fragmentation from hydrodynamic causes and taking into account that the bubble size range relative to the applied frequency and applied acoustic pressure (<90 kPa) excludes the possibility of fragmentation from a Rayleigh-Taylor collapse event (hence also excluding fragmentation from Rayleigh-Taylor instability which is fundamentally the same as PI but originates from a Rayleigh-Taylor collapse or the after-bounce) it becomes clear that the fragmentation we are observing is purely the result of PI activated well above its pressure threshold. As seen in FIGS. 6B and 8C, where an acoustic pressure peak around 50 kPa is applied, significant levels of fragmentation are observed for a relatively large range of bubble diameters in both distilled water and saline solution. At the current acoustic low frequency used, bubble resonance diameter is approximately 500 µm. Many of the bubble sizes investigated are close enough to resonance which explains the relative ease of driving the PI into fragmentation. However, the system is quite effective also in fragmenting the bubbles having diameters between 150 µm and 300 µm which are considerably smaller than resonance size and the increase in surface tension could easily render the technique for these sizes ineffective. A possible explanation for this is the emergence of bubble subharmonic resonance frequencies. As bubbles are acoustically driven beyond the linear regime, additional resonance peaks below their fundamental mode appear. Although not as strong as the fundamental harmonic mode, these subharmonic modes give bubbles below resonance considerable larger oscillation amplitudes than what would be expected from the linear dynamic regime where the bubble retains sphericity. These subharmonic responses become more intense as the acoustic pressure increases and have been reported to appear with acoustic pressures as low as 10 kPa. PI and the appearance of bubble subharmonics have been known to be intimately related and are frequently observed to arise simultaneously. Therefore, it is highly likely that the PI driven bubble fragmentation of bubbles well below resonance size observed here is aided by the appearance of subharmonics which allows for large amplitudes of oscillations that in turn fuels the PI. Additionally, the different exposition times used in the experiments did not seem to affect the fragmentation degree or effectiveness. This is understandable when considering that once the minimum acoustic pressure threshold required for fragmentation is reached, it is considered a typical feature of PI for its amplitude to grow quickly within a few acoustic cycles.

As presented, the device produces an acoustic standing wave (SW) to achieve pressure amplitudes capable of activating PI in bubbles that result in their fragmentation. For this objective, SW has important advantages over a free traveling (FT) acoustic wave. For instance, SW is capable of concentrating acoustic pressure whereas a pure FT wave cannot. The degree of pressure concentration due to a SW can be expressed as the power standing wave ratio (PSWR):

$$PSWR = \frac{I_m}{I_0} \quad (4)$$

where $I_m$ is the maximum SW intensity and $I_0$ is the intensity of the incident wave. We can determine a lower bound for the PSWR of the RAC in the state of acoustic resonance by assuming 100% efficiency from the transducer. For the cases where bubble fragmentation was clearly established, the PZT was powered with 1 W and the area of the PZT was 75 cm². Therefore, the maximum incident acoustic intensity (assuming an efficiency of 1) is 13 mW/cm². $I_m$ can be determined by the acoustic pressure in the bubble fragmentation zone using the relationship:

$$I_m = \frac{P^2}{Z} \quad (5)$$

where P is the acoustic pressure and Z is the acoustic impedance of the medium. For 1 Watt power on the PZT an acoustic pressure of 50 kPa is generated and using the Z value for water of $1.5 \times 10^6$, we obtain a maximum acoustic intensity of 170 mW/cm². Therefore, the PSWR of the RAC is at least 13, meaning that SW conditions can fragment bubbles via PI with about 7% of the energy required to achieve the same result with FT waves. Similar results have been recently reported by W. Secomski, et. al. *In vitro ultrasound experiments: Standing wave and multiple reflections influence on the outcome*. Ultrasonics 2017; 77:203-213, where they attempted to determine the acoustic power required to produce 50% necrosis of glioma cells exposed to an ultrasound field. In their work, 50% less cell viability of glioma cells was obtained using a spatial-average intensity of 5.89 W/cm² in the FT wave case, while the same was obtained with only 0.32 W/cm² when exposed to the ultrasound in SW form; a PSWR of 18 since in both cases 50% cell death was reached at the same acoustic pressure. Moreover, they also determined the acoustic power required to reach a temperature of 43° C. for both FT and SW acoustic field and found that an acoustic power of 1.87 W/cm² was required for FT while 0.32 W/cm² of SW achieved the same thermal effect. This means that for FT acoustic field lethal cell temperature was achieved with less power than that required for cell destruction by cavitation while the opposite was true for the SW case. Hence, to achieve the same peak acoustic pressure SW significantly reduced thermal effects detrimental to cell viability when compared to FT waves.

Finally, since the technique here described establishes the frequency required to generate a SW acoustic field, largely determined by the geometry of the load, many systems such as industrial and medical tubing or even the limb of a biological specimen have dimensions that would require a low-frequency acoustic output to establish a SW. This has some advantages over higher ultrasound frequencies. For example, lower energy requirements, less thermal heating, and capable of producing higher acoustic field intensities without risking initiating inertial cavitation events which can cause structural and biological damage.

Experiments in Swine Thigh

The results obtained in the RAC with distilled and saline solution represent the performance of the device in a system that does not accurately simulate a real biological human limb. Therefore, we purchased freshly cut swine thigh supplied by a local meat distributor. No ethical approval was required as no live animals were used in this study. However, samples were collected directly from the markets following all reasonable aseptic precautions. Sheep blood was purchased from HemoStet Laboratories (Dixon, CA USA).

Six different swine thighs with weights ranging from 15 to 50 pounds were utilized with an artificial artery traversing the swine for bubble injection.

Figure 9:
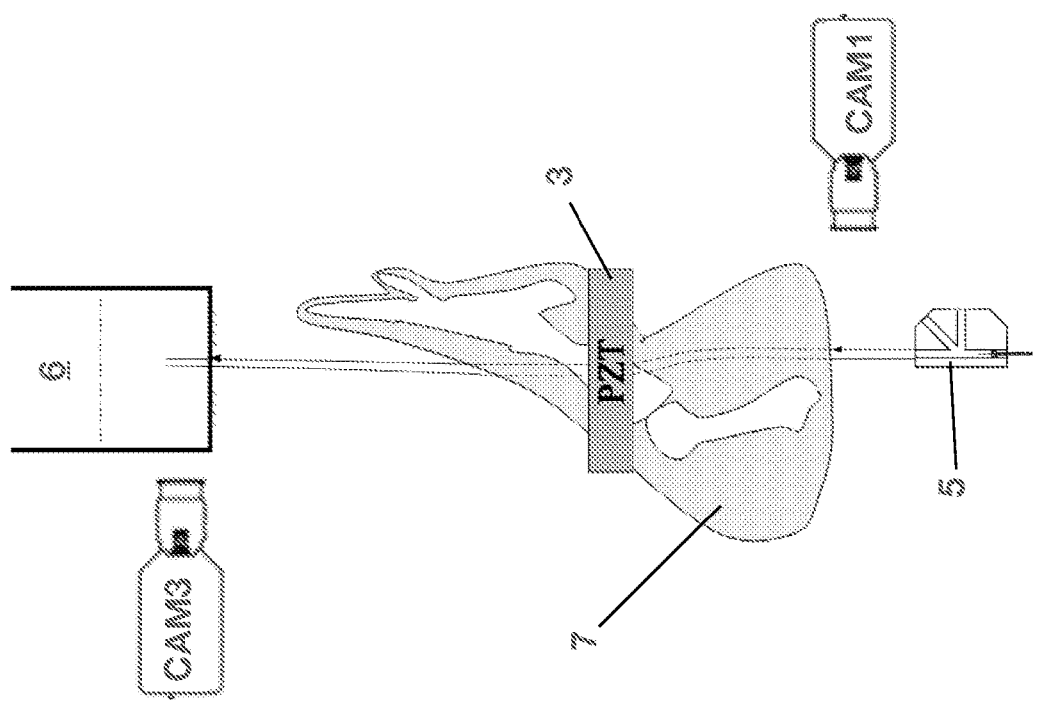
FIG. 9 illustrates the basic setup components of experiments conducted with swine thighs.

Experiments were carried out with the artificial artery filled with saline solution and in other cases with blood. The basic setup is shown in FIG. 9. The artificial artery is attached to the injection system (5) where camera #1 (CAM1) records the injected bubble for size analysis. It extends through the entire swine thigh (7), passes through the PZT (3) region, and attaches to the outlet pool (6) where camera #3 (CAM3) records exiting bubbles.

Figure 10:
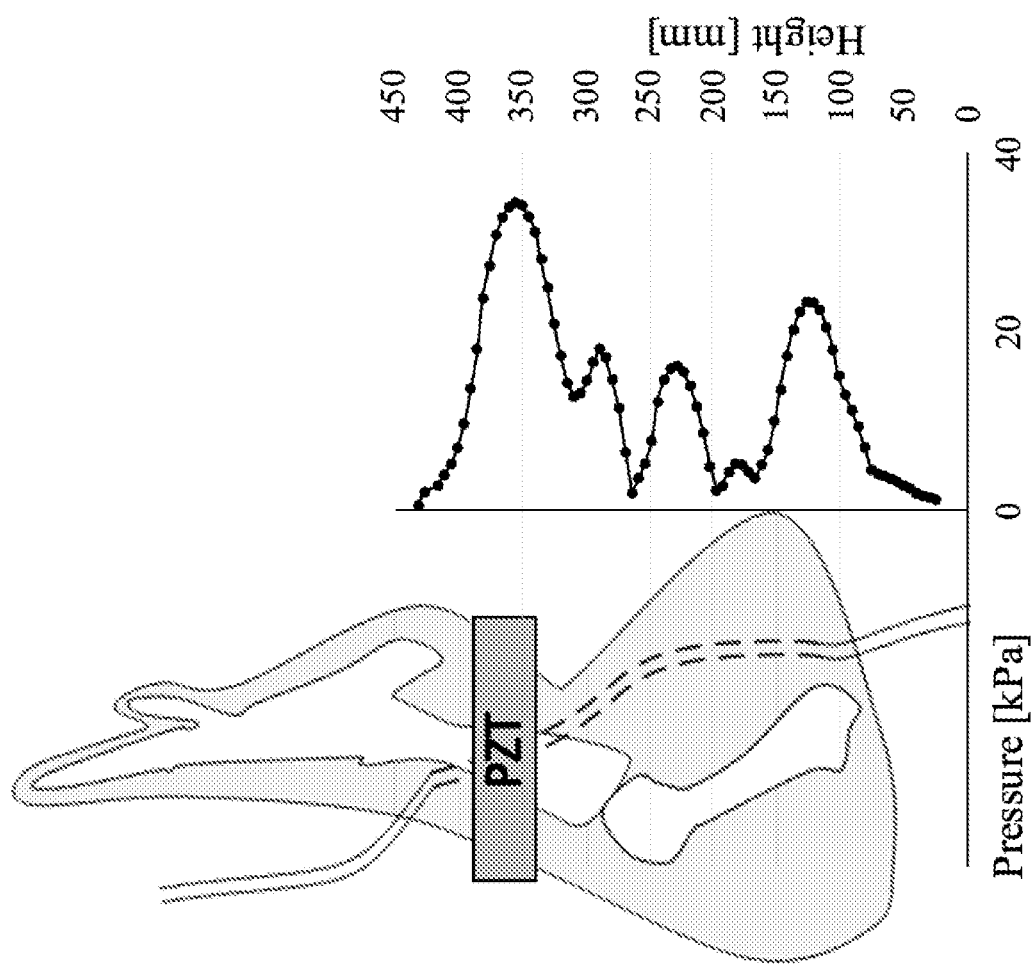
FIG. 10 shows the acoustic pressure measured inside the swine thigh as function of height generated by the powered PZT at the resonant frequency.

Pressure distribution along the swine thigh was measured to determine if it was possible to create the necessary pressure standing wave for bubble fragmentation. In FIG. 10, where the acoustic pressure is plotted as a function of position along the artificial artery in the swine thigh, pronounced anti-nodes (peaks in the graph) and nodes present in the pressure distribution are clearly seen due to the PZT excited at resonance with the swine thigh.

Figure 11:
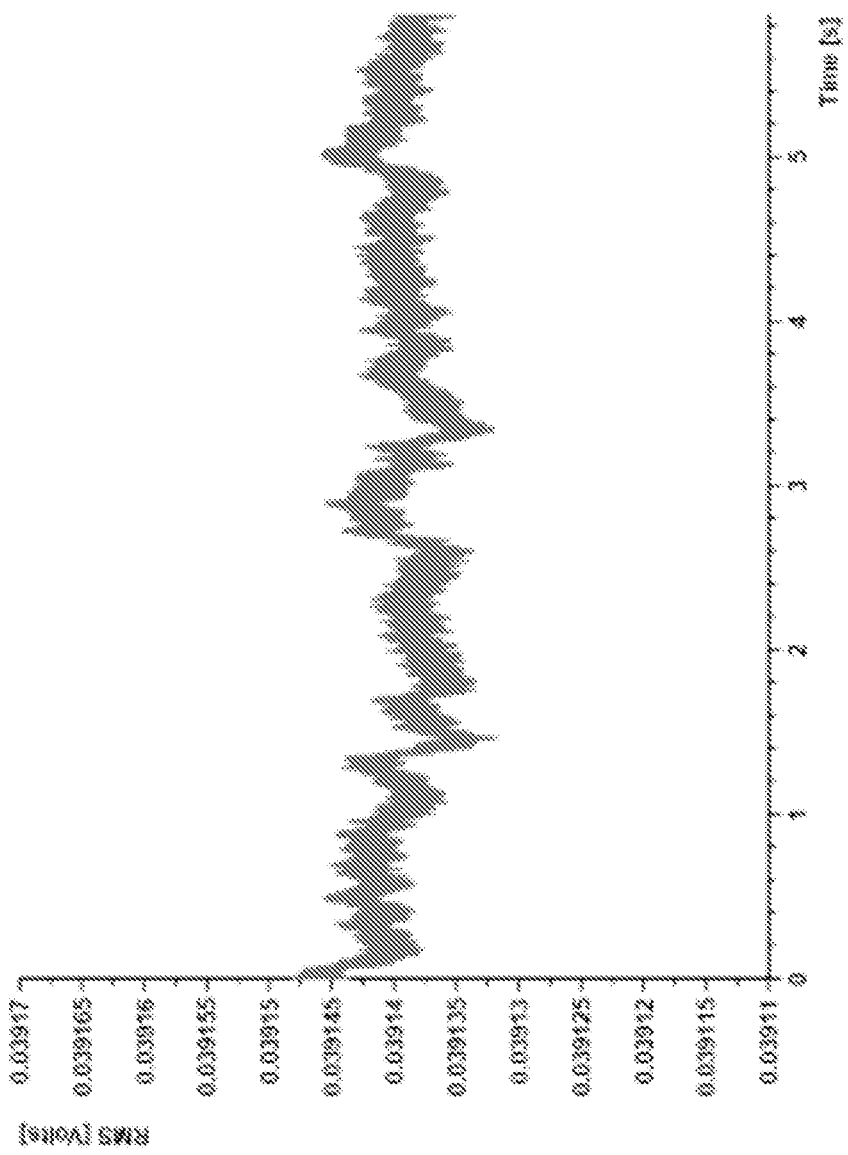
FIG. 11 shows the voltage RMS signal from powered PZT with no bubbles injected into the swine thigh.

One major experimental difficulty when conducting the experiments with the swine thigh compared to experiments performed in the RAC was the loss of visibility of the bubble in motion across the swine. Moreover, there was no visibility in the bubble injection system (CAM1 in FIG. 9) for the experiments using blood instead of saline solution. The simplest solution would be to power the PZT continuously right after the bubble was injected and eventually it would reach the PZT's action region where it would undergo fragmentation. The main issue with this approach is that in the presence of a pressure standing wave, a radiating force, known as the primary Bjerknes force, arises in a bubble traveling through the acoustic field. In our system this force has a component in the radial direction of the artificial artery frequently causing the bubble to attach to the walls of it before reaching the PZT. Other options were explored to overcome the challenges presented due to the loss of visibility, but each one was accompanied by some unacceptable drawback. The effort to overcome the visibility challenge in the swine thigh led us to look at the electric signals (voltage and current) recorded from the PZT. In particular, the root-mean-square (RMS) of the voltage across the PZT while excited at the resonant frequency. The RMS was determined using the moving-window procedure in which the average RMS in a short time interval, or window, is calculated. This window is then shifted to include a new data point and recalculates a new RMS value. This allows to observe the time evolution of the RMS with high resolution. FIG. 11 is an example of the voltage RMS when the PZT is powered with 80 mW and without bubbles present.

Figures 12A, 12B:
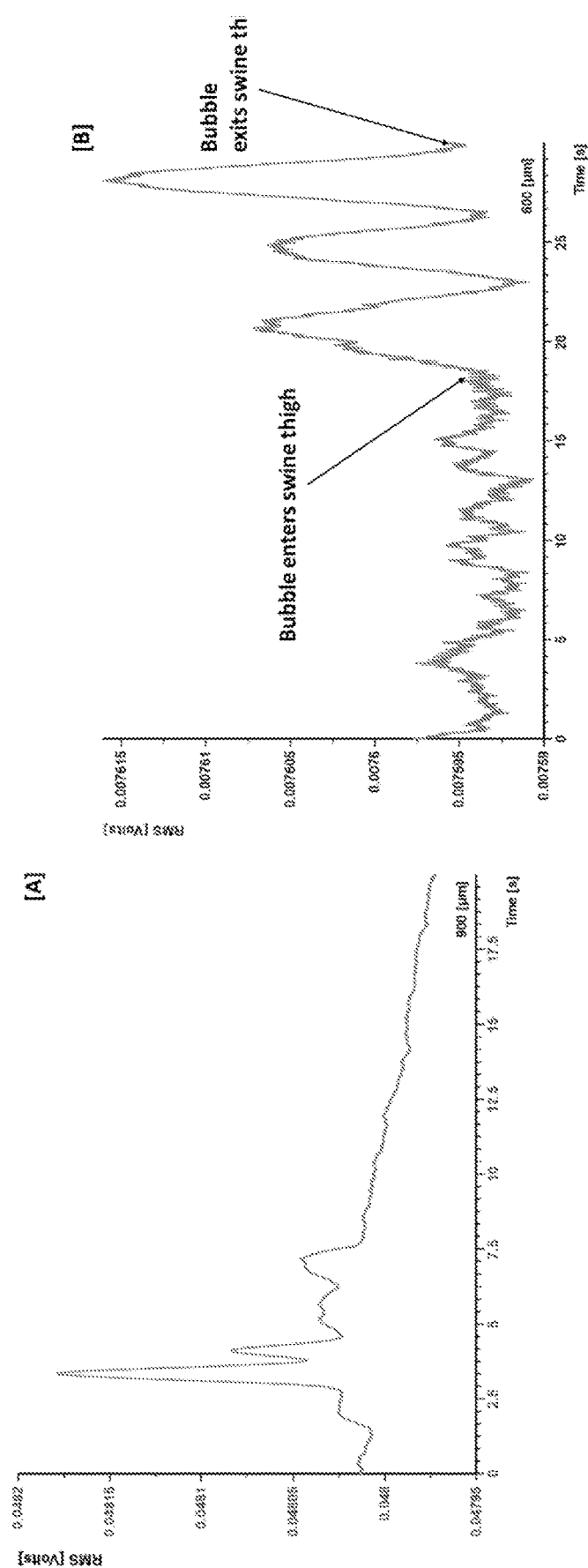
FIG. 12A shows the voltage RMS signal from powered PZT with a 900 µm bubble injected into the swine thigh and artery filled with saline solution.
FIG. 12B shows the voltage RMS signal from powered PZT with a 600 µm bubble injected with blood filling the artificial artery of the swine thigh.

As seen in the figure, the RMS simply fluctuates around some average value. Since 80 mW applied to the PZT proved to be a low enough power to allow an injected bubble to rise by buoyancy nearly unperturbed, we looked for any bubble signature in this RMS signal of the continuously powered PZT as the injected bubble was allowed to travel the swine thigh. FIG. 12A illustrates the bubble signature in the RMS signal when the swine thigh had saline solution inside the artificial artery and FIG. 12B is for the case when blood was used in the artificial artery.

It is clear that a strong signal well above noise level emerges as a result of the bubble traveling across the swine in both saline solution and blood. In this case, a 900 μm bubble was rising through the saline solution and a 600 μm through blood while the PZT was excited at resonance with 80 mW. It was observed that the time at which the signal began to stand out from noise coincide exactly with the moment the bubble entered the swine thigh. Similarly, the time at which the signal died out was exactly the time the bubble exited the swine thigh and was traveling through the tube outside the swine towards the outlet pool. This effect is attributed to perturbance of the pressure standing wave which also extends to cover the length of the entire swine thigh. Interestingly, this phenomenon was not only observed in both saline solution and blood in six different swine thighs, but also for the entire bubble size range under investigation and with powers as low as 0.8 mW. This provided precise knowledge of bubble position within the swine thigh based on the elapsed time from the moment the bubble was generated.

Figure 13:
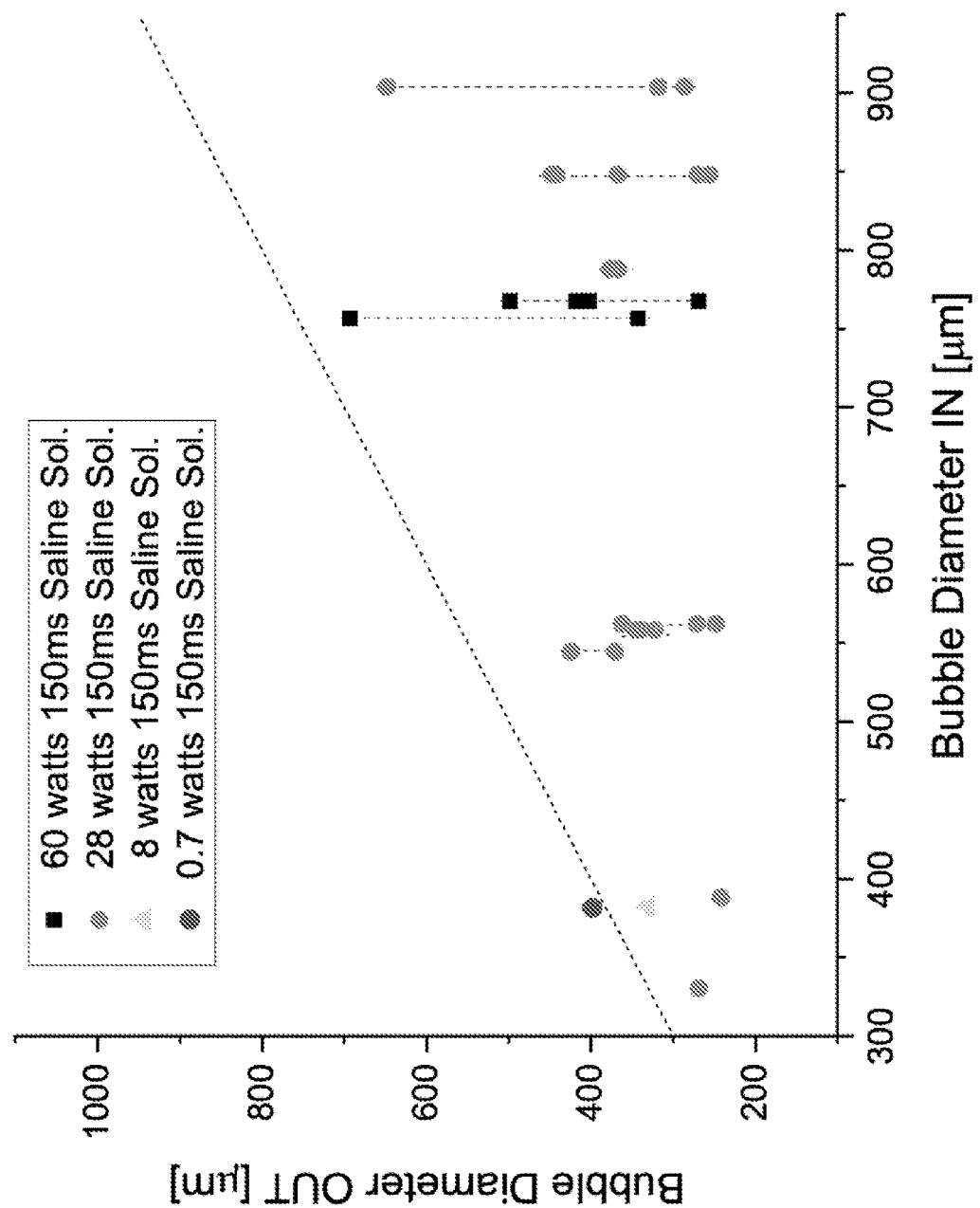
FIG. 13 shows a summary of bubble fragmentation experiments conducted in swine thighs with artificial artery filled with 0.9% saline solution.

Information of the bubble's position within the swine thigh provided by the RMS signal allowed for application of the PZT pulse when the bubble was positioned at a desired location. However, if no bubbles were recorded at the pool outlet by (CAM3) after the PZT pulse was applied it was still unknown whether the reason was complete dissolution of the bubble fragments or if the bubble was attached to the artificial artery by the primary Bjerknes force. Therefore, the point along the swine thigh at which bubble fragmentation was attempted was the one capable of producing fragments large enough to survive until they reached the outlet pool and recorded by (CAM3). Using this method, we were able to fragmentate bubbles in saline solution with diameters between 300 and 900 μm while applying different powers. FIG. 13 summarizes the results obtained from these experiments.

Data points in FIG. 13 below the inclined line represent cases where fragmentation occurred and vertical dashed lines groups fragments from the same original injected bubble. In general, more power is required for bubble fragmentation to occur in the swine thigh than in the RAC. This is expected given that the swine thigh has more losses than the RAC. As seen in FIG. 13, bubbles exposed to the PZT powered at 8 Watts or less produce only negligible size changes in the injected bubble. Significant fragmentation occurs at 28 Watts of power applied to the PZT or above. The results presented were independent of the particular swine thigh used in the experiments. Different swine thighs produced only minor shifts in the resonant frequency which ranged from 17.4 kHz to 17.7 kHz even though the weights varied significantly among the swine used.

As the final feasibility test, we performed swine thigh experiments as the one just described but replacing the saline solution with defibrinated sheep blood in the artificial artery inside the swine thigh. The blood level in the artificial artery was located slightly below the entrance of the outlet pool which was filled with saline solution to preserve visibility of bubbles that exited the swine for (CAM3) recording. It is worth mentioning that the elapsed time, between the moment the bubble crossed the blood-saline solution interphase and the moment it was recorded by (CAM3), was small enough as to avoid any significant changes in size due to differences in viscosity and surface tension. Bubble signal from the PZT electric signal was used again to determine the position of the bubble inside the swine as a function of time. An additional experimental difficulty arising from the blood use in the swine thigh was the loss of visibility of the bubble injected into the system because the interior of the bubble injector was also filled with blood. However, the injection system used produced single bubbles in a highly consistent manner and multiples injections without powering the PZT were performed to establish the baseline bubble size. Once a stable and consistent bubble generation was obtained and recorded, fragmentation attempts with the device were carried out. Additional size analysis of unperturbed bubbles (PZT turned off) was occasionally done between fragmentation experiments to corroborate that our baseline bubble size had not changed. However, the greatest challenge experienced with the blood experiments was being able to detect small, fragmented bubbles since sufficiently small ones may dissolved before reaching (CAM3) view area. Bubbles rising in blood by buoyancy take much longer, by a factor of 2 to 4, to travel the swine compared to saline or distilled water. Which means that any bubble fragments created in blood below 300 μm will require waiting times too high to be recorded by our system. The results obtained in which fragments were produced and observed are presented in FIG. 14. The images at the bottom are frames obtained from (CAM3) at the pool outlet without powering the PZT which established the bubble size baseline. The upper images are the images of the surviving fragments for each reported case.

Figure 14:
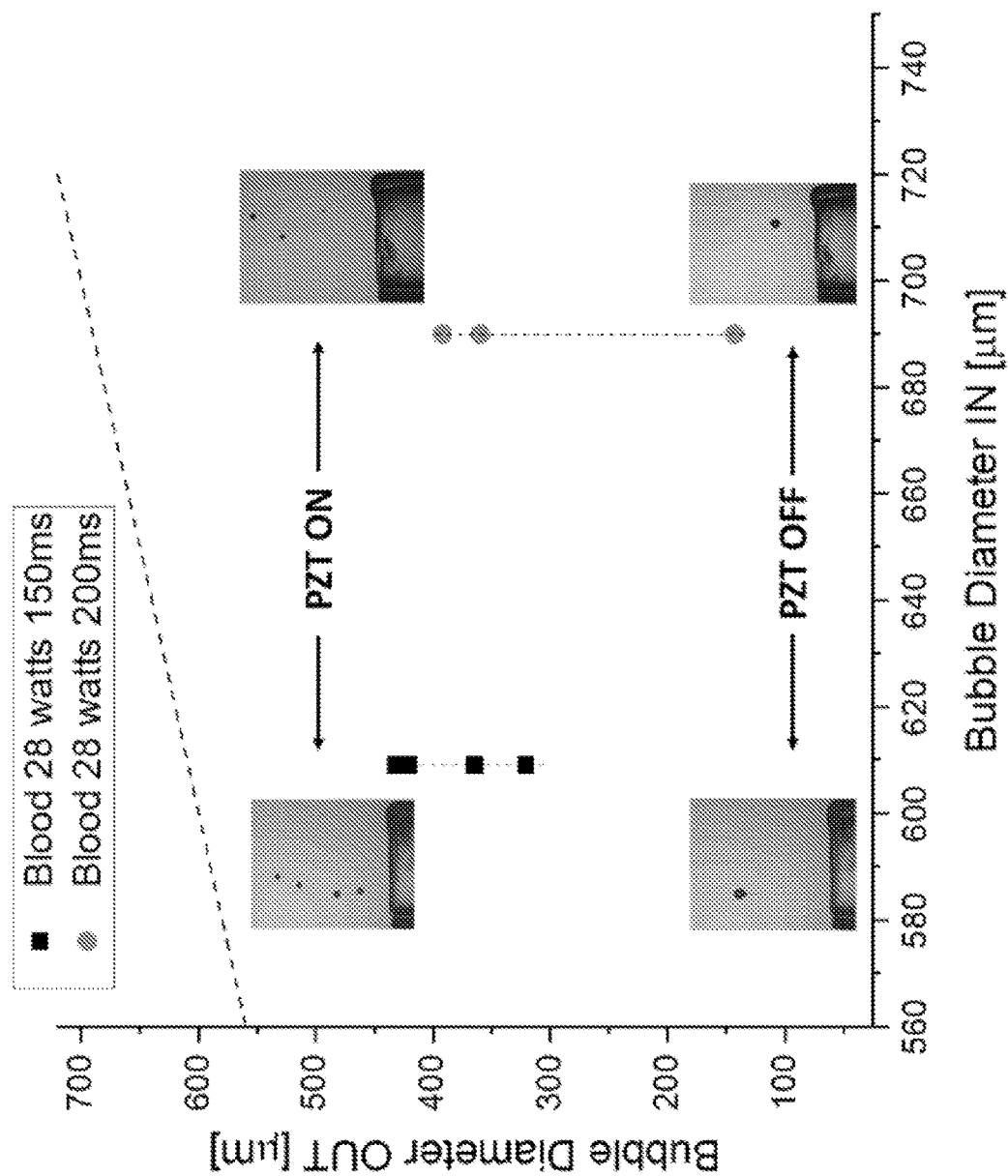
FIG. 14 shows a summary of bubble fragmentation experiments conducted in swine thighs with artificial artery filled with defibrinated sheep blood.

A comparison of the data presented in FIG. 13 (saline solution) with FIG. 14 (blood) shows that similar fragmentation levels occur in blood as in saline solution with the same applied power of 28 Watts and same pulse duration. As previously discussed, fragmentation of a gas-filled bubble in a liquid medium significantly decreases the dissolution time of the gas by increasing the surface-to-volume ratio. Additionally, gas in bubbles is subjected to pressure from the liquid-gas interphase that is inversely proportional to the bubble radius. Therefore, gas in smaller bubbles experiences a greater dissolution driving force than in bigger ones. The device, system and method of the present invention, fragment bubbles of any size in the micro-range, in various liquid mediums, and is able to adapt and perform on different systems, including biological ones.

Determination of the Operational Acoustic Pressure and PZT Power

The Rayleigh Plesset equation (EQ. 3) characterizes well the bubble's volumetric oscillation in an acoustic field as long as the sphericity of the bubble is conserved. However, as the amplitude of the acoustic field is increased surface instability mechanisms are activated and as a result above a certain acoustic pressure threshold the bubble loses its spherical shape and surface waves appear. A theoretical approach that has proven to be useful is to assume a nearly spherical bubble with the surface perturbed only slightly to allow for a linearization of the fluid-dynamical equations around the state of spherical symmetry.

In its most simple form, consider a small non-spherical distortion r of the spherical interface R(t) such that:

$$r(t) = R(t) + a_n(t) Y_n \quad (6)$$

Where R(t) is a solution of equation (1) and $Y_n$ is a spherical harmonic of degree n. The dynamics of the non-spherical distortion amplitude of the bubble is characterized by $a_n(t)$. A potential flow outside the bubble is considered to satisfy the boundary condition such that the velocity at the bubble wall, u, is $u = \dot{R} + \dot{a}_n Y_n$ which is then used in Bernoulli's equation to determine the pressure in the liquid at the bubble wall.

With this taken into consideration, then for the small amplitude case, that is, $|a_n(t)| \ll R(t)$, the linearized fluid-dynamical equations yield a system of mutually uncoupled, linear ordinary differential equations governing the non-spherical perturbations $a_n(t)$ that are parametrically coupled to the radial dynamics R(t):

$$\ddot{a}_n + B_n(t)\dot{a}_n - A_n(t)a_n = 0 \quad (7)$$

where $$A_n(t) = \frac{\dot{R}}{R}(n-1) - \frac{(n-1)(n+1)(n+2)\sigma}{\rho R^3}$$

and $$B_n(t) = 3\dot{R}/R.$$

This simplified model for the characterization of non-spherical perturbations and oscillations neglects viscosity.

Although the model here presented only considers the ideal case with zero viscosity and small perturbations, inclusion of damping effects caused by low non-zero viscosity has been extensively explored by assuming that viscosity effects originate exclusively from a thin liquid layer surrounding the bubble. This "boundary layer" approximation introduces additional terms to the expressions of $A_n(t)$ and $B_n(t)$. Details of this expanded model that introduces viscosity are explained in Prosperetti A. *Viscous Effects on Perturbed Spherical Flow*. Quart Appl Math 1977; 34:339-52; and Hilgenfeldt S, Lohse D, Brenner MP. *Phase diagrams for sonoluminescing bubbles*. Phys Fluids 1996; 8:2808-26, incorporated herein in their entirety. Regardless, just as for the simple case of spherical oscillations (EQ. 3), both the ideal non-spherical perturbation model and its version with the boundary layer approximation are strongly nonlinear and do not admit for analytic solutions, and only numerical approximations can be performed to find solutions of EQ. 7.

Several studies have been performed on the non-spherical perturbations described by EQ. 7 from which regions of spherical stability and instability have been plotted in a Pressure-Radius phase space. In particular, we are interested in the regions of parametric instabilities (PI) that make EQ. 7 unstable where a net growth of non-spherical perturbations occur each cycle of oscillation of period T, so that after several periods the perturbations overwhelms the bubble leading to its fragmentation. Formally, this occurs when the magnitude of the maximal eigenvalue of the Floquet transition matrix $F_n(T)$ is larger than unity. $F_n(T)$ is defined as:

$$\begin{pmatrix} a_n(T) \\ \dot{a}_n(T) \end{pmatrix} = F_n(T) \begin{pmatrix} a_n(0) \\ \dot{a}_n(0) \end{pmatrix} \quad (8)$$

With numerical approximations of $F_n(t)$ and by determining its eigenvalues, the instability zone in terms of bubble size and acoustic pressure can then be identified. As mentioned, there are several reports of such calculations. For example, A. Eller and L. Crum *Instability of the Motion of a Pulsating Bubble in a Sound Field*. J Acoust Soc Am 1970; 47:762-67, incorporated herein in its entirety, determined instability zones in water for acoustic pressures between 30 and 60 kPa and bubble radius ranging 20 to 90 µm under an acoustic field of 25 kHz.

Figure 15:
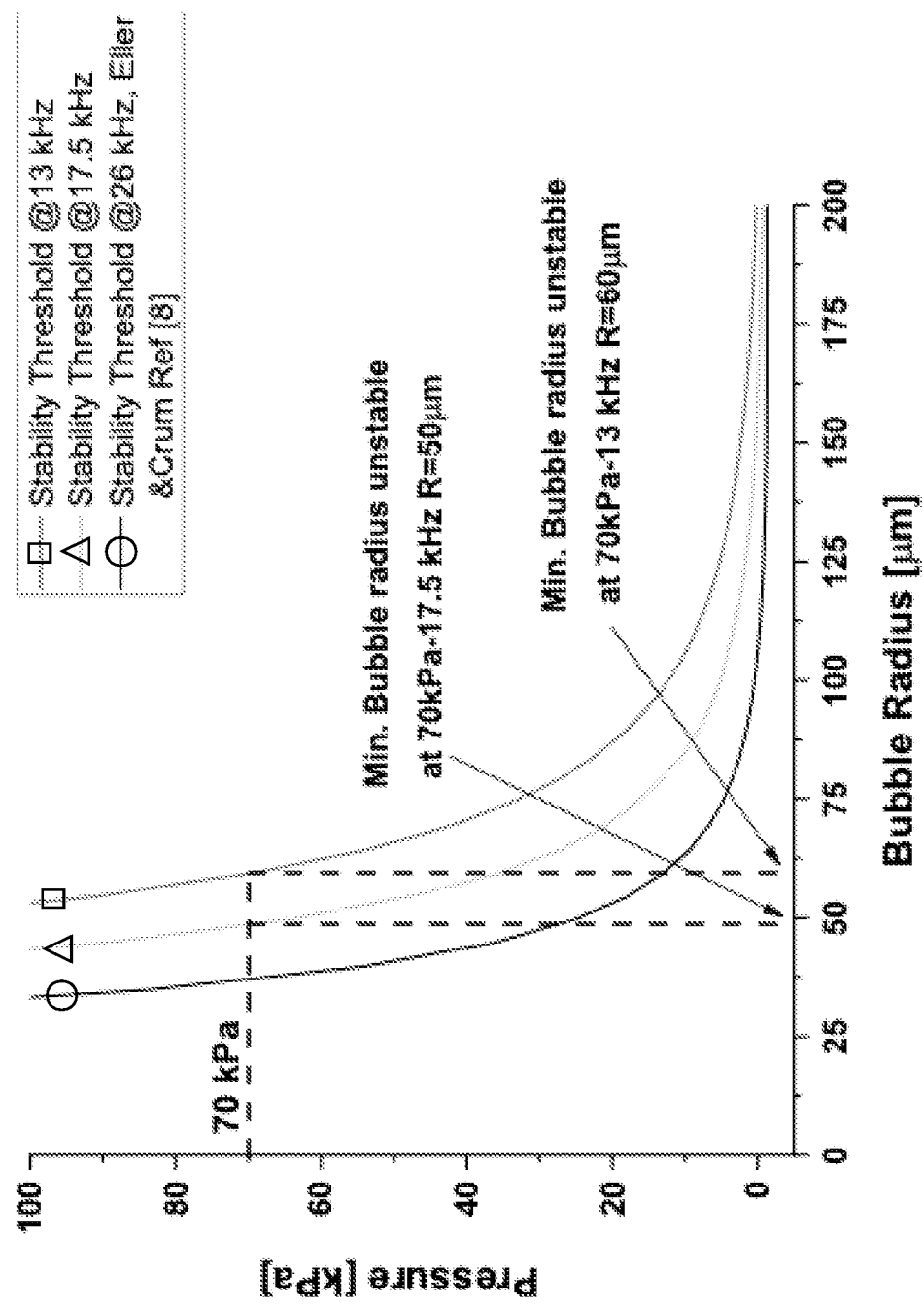
FIG. 15 shows the results of simulation to determine the instability zone in pressure-radius space for a given acoustic frequency, required for fragmentation to occur, where for any particular frequency, all points to the right or above the line is an ordered pair of size and pressure that will likely result in fragmentation.

According to their results, bubbles with radius between 90 and 50 µm were surface instable when the acoustic pressure was 30 kPa or more. Instabilities were present for pressures above 60 kPa regardless of the size. We carried out the numerical approximation applied by Eller and Crum, to extend their results to bubbles sizes of our interest as well as the acoustic frequencies that our device will most likely apply. The results can be seen in FIG. 15, were for the frequencies tested (13 kHz and 17.5 kHz) bubbles with rest radius larger than about 50 to 60 µm will experience the required instability for fragmentation to occur when the acoustic pressure is equal or larger than 70 kPa. These and other theoretical results confirmed what we have observed in our experiments. We have demonstrated that significant bubble fragmentation (40% or more of the initial bubble volume is quasi-instantaneously dissolved) occurs to bubbles with radiuses ranging from 75 to 450 µm when applying between 40 kPa to 67 kPa. These results include applying the technique to geometrical simple systems as well as to unevenly shaped biological specimens like a swine thigh. Therefore, we conclude that 70 kPa is the acoustic pressure target that will effectively and significantly accelerate the bubble dissolution rate in a bubbly fluid by fragmentation in a wide range of applications and systems.

Bio applications of the device, such as bubble fragmentation on a human thigh or in blood lines of hemodialysis machines, needs to consider safety issues. For this purpose, the FDA applies the concept of Mechanical Index (MI) to estimate the risk of initiating violent cavitation events in blood and tissue when applying technologies based on ultrasound. MI can be determined by the following equation:

$$MI = \frac{P}{\sqrt{f}} \quad (9)$$

where P is the maximum negative pressure at the antinode of the standing wave in MPa and f is the acoustic frequency in MHz. FDA requires an MI not greater than 1.9. Throughout the variety of systems tested, the lowest observed resonance frequency was 13 kHz. From EQ. 9, it is clear that for a given acoustic pressure, reducing the applied frequency will increase the MI. Since our target is 70 kPa of acoustic pressure, using a resonance frequency of 13 kHZ, the high range of MI we would observe in applying the device would be 0.6. This is well below the 1.9 limit imposed by the FDA.

Now, the operating parameter controlling the antinode intensity of the acoustic standing wave is the voltage applied to the PZT. In order to determine the voltage applied required to generate a 70 kPa acoustic pressure in the system under treatment, the pressure per volt applied (P/V) value needs to be determined. The P/V value for the artificial thigh system and the swine thigh (biospecimen) of the experiment was between 1.6 and 1.8 kPa per rms volt applied. Therefore, for most potential applications, a rms voltage between 39V and 44V will suffice to produce significant bubble fragmentation. However, depending on the applications and its conditions, a different voltage might be required. For this reason, the specific power to be applied should be certified by numerical simulations using the COMSOL Multiphysics® software (COMSOL, Inc., Burlington, MA USA).

We have previously reported on our numerical simulations of acoustic fields in acoustic chambers (Valentin, F I, Cancelos, S. *Predicting Bubble Migration due to Bjerknes Force in a Complex 3D Geometry: Numerical and Experimental Results*. Proceedings of the ASME 2012 Volume 2: Fora. 2012; pp. 223-232, incorporated herein in its entirety), therefore a brief description of the general governing equations applied to the main mechanical domains in the simulation will be explained below.

In the case of the artificial thigh system, the main coupled domains compromising the system are the fluid, the elastic solid components (glass, acrylic flanges, etc) and the PZT. Subjected to a harmonic excitation, $p'=\bar{p}(r)e^{j(\omega t)}$, in the fluid domain, the well-known Helmholtz equation is solved:

$$\nabla^2 p' - \frac{1}{\rho c^2} \frac{\partial^2 p'}{\partial t^2} + \lambda \frac{1}{\rho c^2} \nabla^2 \frac{\partial p'}{\partial t} = 0 \tag{10}$$

where, $\lambda$ is the is the coefficient of dilatational viscosity determined by the shear and bulk viscosity of the fluid, and $\rho_0$ and c denote the fluid density and the speed of sound in the fluid, respectively. The assumptions made in this domain are that only small perturbations are produced, and the fluid is lossless, performs irrotational flow, and undergoes isentropic processes only. The solid components of the system, except for the PZT, are considered elastic, therefore in the small perturbation regime the stress-strain relationship is governed by Hooke's Law and is expressed as:

$$\underline{\underline{T}} = \underline{\underline{\hat{c}}} : \underline{\underline{S}} \tag{11}$$

where T represents Cauchy's stress tensor, c is a fourth-order elasticity tensor and S is the strain tensor. The number of lines underneath indicate the order of the tensor. It is important to note here that, since this is the component of the system that could mostly vary depending on the application, other models might have to be invoked depending on the particularities of a specific application. In this case, since only perturbations of small amplitude are assumed present, a complex time-harmonic solution u can be applied leading to the homogeneous Helmholtz equation governing the dynamics of the elastic solid domain:

$$-\rho \omega^2 \underline{u} - \nabla \cdot \underline{\underline{T}} = 0 \tag{12}$$

where $\rho$, $\omega$, denote structural density and angular frequency.

The piezoelectric material obeys a symmetric mechanical-electrical energy conversion relationship expressed in the piezoelectric constitutive equations, which essentially couples the acoustic field equations with Maxwell's electromagnetic field equations. The constitutive equations for the stress T and electric displacement D in the modeled PZT are:

$$\underline{\underline{T}} = \underline{\underline{\hat{c}}}^E : \underline{\underline{S}} - \underline{\underline{e}} \cdot \underline{E} \tag{13a}$$

$$\underline{D} = \underline{\underline{e}} : \underline{\underline{S}} + \underline{\underline{\hat{\varepsilon}}}^S \cdot \underline{E} \tag{13b}$$

Where T is the stress field, S is the strain field, E is the electric field, D is the electrical displacement field, c is the elasticity matrix (four order stiffness tensor), e is the third order piezoelectric stress tensor, ε is the second order permittivity tensor of the material and superscripts S and E denote properties measured at constant stress and electric field respectively.

Continuity requirements at interphases of elements were applied as boundary conditions. In the case of the fluid-solid interphase, continuity of displacement was invoked and expressed in terms of acoustic pressure, p, in the fluid and the normal acceleration, $a_n$, of an element of the elastic solid in contact with the fluid:

$$a_n = -\underline{n} \cdot \left(-\frac{1}{\rho_0} \nabla p\right) \tag{14}$$

For solid-solid component boundary, continuity of displacement and stress was applied:

$$(\underline{u})_1 = (\underline{u})_2 \tag{15a}$$

$$(\underline{\underline{T}})_1 \cdot \underline{n} = (\underline{\underline{T}})_2 \cdot \underline{n} \tag{15b}$$

where u is the displacement vector of the material, T the stress tensor in the material, and n is the vector normal to the interface.

COMSOL Multiphysics software solves these sets of equation providing among other things the P/V value, required to determine the exact voltage that should be applied for a given application in order to obtain the target value of 70 kPa.

According to another embodiment of the invention, the operational acoustic pressure and associated PZT power can also be determined on-site and/or real time by determining the presence and size of bubbles while power is being simultaneously applied to the PZT piezoelectric device. On such system that can be used to achieve this is disclosed on patent U.S. Pat. No. 10,376,244 B1 issued on Aug. 13, 2019 to Cancelos, et al., incorporated herein in its entirety. As can be understood, once the PZT piezoelectric device is tuned to the resonant frequency of interest, the PZT piezoelectric device is provided with an initial voltage and the presence, amount and size of bubbles is monitored. Then, the voltage provided to the PZT piezoelectric device is selectively changed until bubble fragmentation is determined by measuring the presence, amount, and size of the bubbles.

CONCLUSIONS

The invention proposes a bubble fragmentation acoustic technique based on resonance. Bubble fragmentation drastically decreases the time required for its dissolution by increasing its surface-to-volume ratio. The technique utilizes the reciprocity principle to non-invasively determine the acoustic frequency required to establish a state of mechanical resonance and the formation of an acoustic pressure SW. It was shown that the resulting SW generated within the system used for investigating the technique, the RAC, concentrated the acoustic pressure, providing a region with at least 13 times more acoustic intensity when compared to an equivalent FT wave. This capability to focus acoustic pressure allows to excite bubbles well beyond the linear regime where PI could be fueled producing the fragmentation event. Additionally, the acoustic pressure achieved is also within the range of intensities where bubble sub-harmonic frequencies emerge allowing the technique to produce bubble fragmentation in bubbles with radius considerably smaller than what would be expected from linear models of bubble dynamics.

Finally, the technique of the invention is energy-efficient, effective in achieving the state of mechanical resonance in a complicated load even with anti-symmetric elements such as the simulated bone, easy to recalibrate, and with reduced adverse effects such as less heating and less risk of initiating cavitation events when compared to ultrasound FT waves.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

We claim:

1. A method for increasing the gas-dissolution rate of bubbles in blood flowing in an artery within a thigh and said artery within a thigh forming an enclosed volume, said method comprising the steps of: determining a resonant frequency of said artery within a thigh forming the enclosed volume; using a piezoelectric transducer applied as a single emitter/receiver unit and the reciprocity principle to determine the resonant frequency wherein said piezoelectric transducer is applied at a power level of 28 watts for a time selected from or between 150 ms to 2000 ms; and generating within said artery within a thigh forming the enclosed volume an acoustic pressure at said resonant frequency that fragments bubbles flowing in said blood thereby effectively increasing the gas-dissolution rate of said bubbles in said blood.

2. The method according to claim 1, wherein said resonant frequency is determined based on voltage and current measurements of a piezoelectric transducer at the electrical terminals of said piezoelectric transducer during a frequency sweep when said piezoelectric transducer is in contact with said thigh forming the enclosed volume.

3. The method according to claim 1, wherein the acoustic pressure is generated by said piezoelectric transducer that is supplied with a voltage, said piezoelectric transducer being in contact with said thigh forming the enclosed volume.

4. The method according to claim 3, wherein said voltage is calculated based on a pressure per volt applied to said thigh forming the enclosed volume as determined by the piezoelectric transducer used and said thigh forming the enclosed volume containing said blood.

* * * * *